United States Patent
Klösel et al.

(10) Patent No.: US 6,281,371 B1
(45) Date of Patent: Aug. 28, 2001

(54) LIPOPOLYAMINES, AND THE PREPARATION AND USE THEREOF

(75) Inventors: Roland Klösel; Stephan König, both of München (DE)

(73) Assignee: Biontex Laboratories GmbH, Munich (DE)

(*) Notice: Subject to any disclaimer, the term of this patent is extended or adjusted under 35 U.S.C. 154(b) by 0 days.

(21) Appl. No.: 09/463,172

(22) PCT Filed: Aug. 13, 1998

(86) PCT No.: PCT/EP98/05156

§ 371 Date: Mar. 29, 2000

§ 102(e) Date: Mar. 29, 2000

(87) PCT Pub. No.: WO99/08997

PCT Pub. Date: Feb. 25, 1999

(30) Foreign Application Priority Data

Aug. 13, 1997 (DE) ............................................. 197 35 125
Jul. 31, 1998 (DE) ............................................. 198 34 683

(51) Int. Cl.$^7$ .................................................. C07C 233/00
(52) U.S. Cl. .......................... 554/51; 554/104; 564/192; 564/193; 564/403; 564/511; 564/512; 514/625; 514/626; 424/450
(58) Field of Search ...................... 554/51, 104; 564/192, 564/193, 463, 511, 512; 514/625, 620; 424/450

(56) References Cited

FOREIGN PATENT DOCUMENTS

| 196 3189 | 6/1971 | (DE) . |
| 196 07686 | 9/1997 | (DE) . |
| 039411 | 10/1990 | (EP) . |
| 0535576 | 4/1993 | (EP) . |
| 0544292 | 6/1993 | (EP) . |
| WO 9011092 | 10/1990 | (WO) . |
| WO 9116024 | 7/1991 | (WO) . |
| WO 9303768 | 3/1993 | (WO) . |
| WO 9405623 | 3/1994 | (WO) . |
| WO 9421808 | 9/1994 | (WO) . |
| WO 9601840 | 1/1996 | (WO) . |
| WO 9601841 | 1/1996 | (WO) . |
| WO 9618372 | 6/1996 | (WO) . |
| WO 9640264 | 12/1996 | (WO) . |
| WO 9640265 | 12/1996 | (WO) . |
| WO 9640725 | 12/1996 | (WO) . |
| WO 9640726 | 12/1996 | (WO) . |
| WO 9641873 | 12/1996 | (WO) . |
| WO 9700241 | 1/1997 | (WO) . |
| WO 9703939 | 2/1997 | (WO) . |
| WO 9746233 | 12/1997 | (WO) . |
| WO 9802191 | 1/1998 | (WO) . |

OTHER PUBLICATIONS

J.P. Behr et al., Bioconjugate Chem. 5.382–389 (1994).
P.L. Felgner et al., Proc. Natl. Acad. Sci. USA 74, 7413 (1987).
Liposome Technology, Gregoriadis, CFC Press N.Y. 1984.
Liposome, Ostro, Marcel Dekker, N.Y. 1987.
Lichtenberg et al., Methods Biochem. Anal. 33, 337–462 (1988).
Pagano and Weinstein et al., Ann. Rev. Biophysic. Bioeng. 7, 435–568 (1978).
Szoka and Papahadjopoulos et al., Ann. Rev. Biophysic. Bioeng. 9, 467–508 (1980).
J.P. Behr et al., Proc. Natl. Acad. Sci. USA 86, 6982 (1989).
Byk et al., J. Med. Chem. 41, 224 (1998).
Radler et al., Science, 275, 810 (1997).
Remy, Jean et al., Bioconj. Chem. ˆ(6), 647 (1994).
Behr J.P. et al., Gene Therapy, 3, 1010 (196).
F.W. Anderson, Science, 256, 808 (1992).
Science 258, 744 (1992).
Wu et al., J. Chem. 262, 4429 (1987).
Wang et al., Proc. Intern. Symp. Control. Rel. Bioact. Mater., 22, 414 (1995).

*Primary Examiner*—Deborah D. Carr
(74) *Attorney, Agent, or Firm*—Pitney, Hardin, Kipp & Szuch, LLP

(57) ABSTRACT

The present invention relates to new lipopolyamines (including salts thereof) characterised by a symmetrical, highly flexible lipophilic moiety having buffering capacity at physiological pH, and to the use thereof for the in vivo or in vitro introduction of biologically active materials, such as, for example, DNA, RNA, ribozymes, antisense DNA, PNA, peptides and proteins, into eukaryotic cells.

14 Claims, No Drawings

LIPOPOLYAMINES, AND THE PREPARATION AND USE THEREOF

This application is a 371 of PCT/EP98/05156 filed Aug. 13, 1998.

Positively charged lipids (J. P. Behr, Bioconjugates Chem. 5,382–389, 1994) are used in the form of liposomes, micelles or per se, for the introduction of biologically active substances, such as peptides, peptoids, proteins, PNA and antiviral active substances, but especially DNA, RNA, antisense DNA/RNA or ribozymes, into eukaryotic cells (for example mammalian, plant or insect cells). Lipopolyamines are a special class of cationic lipids that exhibit comparatively outstanding transfection properties. "Transfection" is to be understood as meaning the introduction of hereditary material into eukaryotic cells.

The need to introduce DNA (for example plasmids, cosmids, single-stranded or double-stranded), RNA or related classes of substances, such as antisense DNA/RNA or ribozymes, into eukaryotic cells in order to be able, for example, to carry out gene therapy successfully, has led to the development of numerous transfection methods. A large number of methods are known for the introduction of nucleic acids into eukaryotic cells, especially mammalian cells, such as, for example, the $CaPO_4$ precipitation method, the DEAE/dextran method, synthetic polyamines (polyethyleneimine, polylysine, PAMAM dendrimers), methods that use receptor-mediated endocytosis, electroporation, microbombardment, microinjection and methods that use viral capsids as DNA carriers. A further method is termed "lipofection" (P. L. Felgner et al., Proc. Natl. Acad. Sci. USA 74, 7413 1987) which makes use of the fact that synthetic cationic lipids, in the form of liposomes, micelles or per se, form complexes with negatively charged DNA. By so adjusting the relative amounts of DNA and cationic lipid to produce complexes having a net positive charge, the complexes obtained have a high affinity for the negatively charged membrane surface of eukaryotic cells. When such DNA/lipid complexes contact cells, the introduction of the genetic material into the cell results. The exact mechanism by which the DNA gets into the cells is still largely unknown, but it is assumed that either fusion of the cationic lipids with the anionic cell membrane occurs, with simultaneous delivery of the DNA into the interior of the cell, or that the DNA/lipid complexes pass in their entirety into the cell by means of a natural transport mechanism of the cells, so-called endocytosis, and the DNA is then released.

Liposomes are, as a rule, spherical arrangements of lipids in aqueous solutions having a "bilayer structure" and are typically divided into three classifications (see N.Y. Academy Sciences Meeting: "Liposomes and their use in Biology and Medicine", December 1977): multilamellar vesicles (MLV, up to 10,000 nm), small unilamellar vesicles (SUV, 20–50 nm) and large unilamellar vesicles (LUV, 600–30,000 nm). A number of methods for the production of liposomes is known and these are described in "Liposome Technology" (Gregoriadis, CFC Press, New York 1984), in "Liposomes" (Ostro, Marcel Dekker, New York 1987) or in review articles by Lichtenberg et al. (Methods Biochem. Anal. 33, 337–462, 1988), Pagano and Weinstein (Ann. Rev. Biophysic. Bioeng. 7, 435–468, 1978) or Szoka and Papahadjopoulos (Ann. Rev. Biophysic. Bioeng. 9, 467–508, 1980). Known methods include, for example, the "reverse-phase evaporation" method and the extrusion method, in which a lipid solution is pressed through a microporous membrane. Liposomes are typically also prepared in the following manner: the lipids are taken up in an organic solvent By vaporisation of the solvent under a stream of nitrogen, a thin film of lipid is produced on the wall of the glass vessel. The addition of water or aqueous buffer solution hydrates that film. The solution obtained is finally treated with ultrasound.

Cationic lipids are becoming increasingly important in gene therapy. In such therapy, body cells are transfected in vivo by various methods, by administering complexes of carrier and DNA intradermally, intramuscularly, intraperitoneally, intravenously, subcutaneously, intranasally, into fluid spaces or directly into tumours, or by removing, transfecting and reimplanting body cells. Until some time ago, a favoured method was the introduction of the genetic material by viral carrier, but that method carries the risk of retromutation to a pathogenic virus. Furthermore, the DNA introduced is stably incorporated into the genotype, so it is not possible to control the therapy or to return the cells to their original state. In addition, viral carriers have restrictions regarding the size of the DNA to be introduced. Modified DNA or RNA is not transferred by viruses. Also, only dividing cells can be transfected by that method.

Other risks to be considered when using viral carrier systems are the possible activation of oncogenes and an immune reaction of the treated organism.

Transfection with cationic lipids, on the other hand, is not subject to those restrictions. The transfection is usually transient, that is to say, the transfected DNA or RNA is expressed only for a certain period, since it is not incorporated in the genotype and over time is degraded by nucleases. In that way gene therapy can be measured and made reversible. There are no restrictions in terms of the size of the DNA and, in addition, it is also possible by means of cationic lipids to introduce modified DNA or RNA (for example antisense DNA/RNA, or ribozymes stabilised by the incorporation of modified nucleotides) into cells. Also, non-dividing cells, such as, for example, nerve cells, can be transfected by cationic lipids.

Furthermore, cationic lipids have not so far been found to have any immunogenic behaviour in in vivo tests.

While the in vivo use of microinjection and electroporation does not appear possible for process-related reasons, the $CaPO_4$ and DEAE/dextran methods exhibit poorer transfection efficiency compared with lipofection.

The cationic lipids include a class of lipids, so-called lipopolyamines, that utilizes the known high affinity between polyamines (for example spermine, spermidine) and DNA for transfection. The polyamines in that class of lipids have a linear or branched structure and contain ethylene, propylene or butylene groups between the amino functions. The polyamines are bound in a wide variety of manners to a lipophilic radical.

For example, spermine, which is positively charged at physiological pH, is linked to a hydrophilic radical in some cases by way of a spacer. Spermine forms stable complexes with DNA and similar compounds by being bound in the groove of the DNA by hydrogen bridge bonding. The first such lipospermnine derivatives were synthesised by Behr, J. P. et al. (Proc. Natl. Acad. Sci. USA 86; 6982–6986; 1989; EP 0 394 111). In that process carboxyspermine was linked by way of a spacer to two different hydrophilic radicals. The structure of the resulting 5-carboxyspermylglycinedioctadecylamide (DOGS) is as follows:

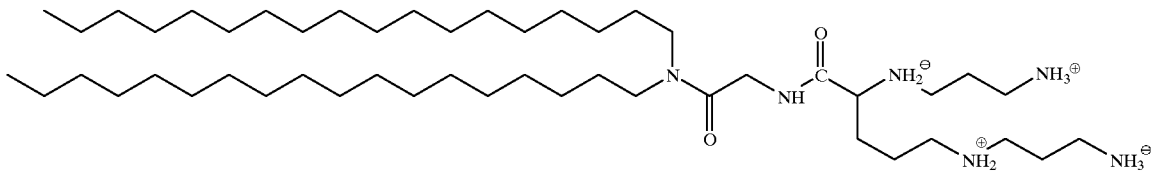

DOGS is available commercially as Transfectam™ (Promega). The second compound developed by Behr et al. is dipalmitoylphosphatidylethanolamine-5-carboxyspermylamide (DPPES):

In WO 97/00241, von Der Eltz et al. describe the compound 2-(6-carboxyspermyl)-1,3-dioleoyloxypropylamide, which has been marketed under the name DOSPER (Boehringer Mannheim GmbH):

A further lipospermine derivative is claimed by P. L. Felgner et al. in WO 91/16024 under the name L-spermine-5-carboxy-3-(DL-1,2-dioleoyldimethylaminopropyl-β-hydroxyethylamine). In the Patent Specification, however, L-spermine-5-carboxyl-3-(DL-1,2-dipalmitoyldimethylaminopropyl-β-hydroxyethylamine) is described:

In WO 94/05624, Gebeyehu, G. et al. describe the compound N-[N-(5-carboxyspermyl)aminoethyl]-N,N-dimethyl-2,3-bis(9-octadecenyloxy)-1-propaneammonium tetra(trifluoroacetate), which is available commercially as Lipofectamin™ (Gibco-BRL: Life Technologies Inc.):

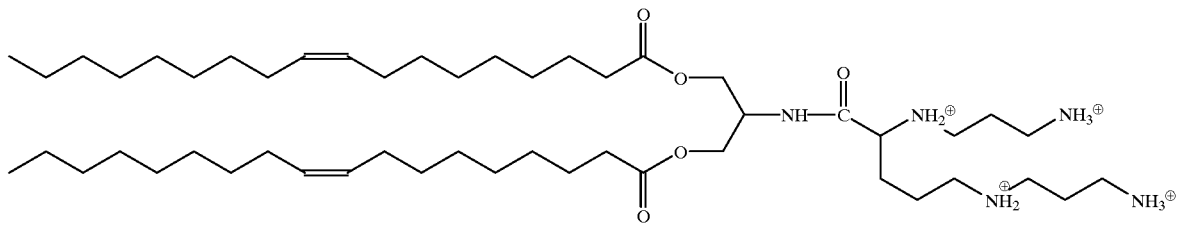

The compounds mentioned so far were all prepared by amide or ester linkage of a linear polyamine carrying a carboxy function as side chain, i.e. by linkage of carboxyspermnine, to a lipophilic radical. Later publications disclose other methods of linking linear polyamines to the lipophilic radicals, for example by amide or carbamate linkage to a terminal amino function (linear structure) or inner amino function ("T-shape-structure") of the linear polyamine. Examples may be found in the following publications: DE 1 963 189, WO 96/40726, WO 96/40725, WO 96/18732, WO 97/46223, WO 98/02190 and WO 98/02191. Branched polyamines have also been described (G. Byk et al., J. Med. Chem., 41, 224–235, 1998).

Despite great advances in the field of transfection using cationic lipids, there is still a need for a larger choice of such lipids. The reason for that is that, to date, no cationic lipid has been found that yields satisfactory results with all cell types. Since different cell types differ in their membrane composition, it is not surprising that various compositions of lipids and a variety of types of lipid are required for an effective transfection of different cells.

Since there is still little known so far about the actual transfection process, the development of new cationic lipids is substantially empirical. Important aspects for consideration for the design of such lipids should therefore be their physical properties in terms of the formation of liposomes or micelles, the properties of the liposomes or micelles formed, the toxicity towards the target cells to be transfected, and furthermore the stability of the lipids, their propensity to be metabolised and the possibility of in vivo use.

The problem to be solved according to the invention is accordingly to find new cationic lipids that have a high degree of activity and the broadest possible spectrum of activity combined with good stability and low toxicity. In the case of the present invention it has now, surprisingly, been found that the combination of polyamines as head group with a specific lipophilic radical results in especially good properties in terms of efficiency and stability:

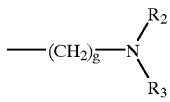

The radicals R are saturated or unsaturated, linear or branched alkyl chains, preferably having from 10 to 20 carbon atoms.

The following hypotheses may be used as an explanation. The formation of a so-called DNA/lipid complex has proved to be of particular importance for successful transfection. When DNA and cationic lipids that are used in the form of liposome or micelle formulations meet, spontaneous condensation of the DNA occurs with collapse of the liposomal or micelle-type organisation structure of the cationic lipids. A DNA/lipid complex forms in which the DNA is embedded in a multilamellar complex of the said lipids that has a bilayer structure (J. O. Rädler et al. Science, 275, 810, 1997). Once, for example, the spermine group, as head group with DNA affinity, has been bound to the DNA, then the flexibility and symmetry of the remainder of the molecule moiety (lipophilic radical) becomes especially important, since the alkyl groups must be capable of alignment that is as far as possible parallel in order to be able to form stable "bilayer structures" by way of van der Waals forces.

Generally, the structure of the compounds proposed hitherto is not very symmetrical, making a parallel alignment of the alkyl radicals difficult, and every one of those compounds contains ester, ether or amide linkages between the alkyl radicals and a skeletal structure or a spacer, as the case may be. Those compounds are accordingly severely restricted in their flexibility in view of the fixed bond angle and, in the case of amide linkages (for example in compounds from G. Byk. et al., J. Med. Chem., 41, 224–235, 1998, EP 0 394 111, WO 96/18372, WO 97/46223, WO 98/02190 and WO 98/02191), in view of the resonance structures present.

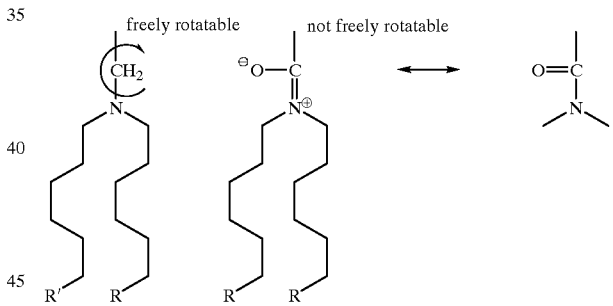

In the resonance structure for amides, the oxygen atom carries a negative charge and the amide nitrogen atom a positive charge. The result is a planar arrangement of the atoms involved in the amide bond. A free rotation of the amide bond between carbonyl carbon and the nitrogen atom is not possible. This feature has, for example, a very special effect on the structure of proteins (secondary, tertiary and quaternary structure), of which the peptide bonds are nothing more than amide linkages. It is not until the rigid, non-flexible amide linkages are present that the protein is given its biologically necessary structure.

The compounds according to the invention (see also below) link the alkyl radicals $R_2$ and $R_3$ by way of a tertiary nitrogen atom (amine). This ensures a high level of symmetry and, as a result of it being possible for the free pair of electrons at the nitrogen atom to "swing through" (pseudorotation), maximum flexibility. There therefore exists in those compounds the optimum prerequisite for parallel alignment of the alkyl radicals (despite head groups which are securely anchored to the DNA) and consequently for the formation of stable DNA/lipid complexes. The stability is provided especially also by a large degree of overlap between the van der Waals regions of the alkyl groups.

A further possible explanation for the especially good properties of the claimed compounds is that since the basic nitrogen atom, which carries the alkyl radicals, is not involved in the DNA complex formation, the compounds have buffering capacity in the physiological pH range. That characteristic promotes the osmotic breakdown of the endosomes during the endocytosis process, so that there is improved release of the DNA into the cytosol (J. P. Behr, Gene Therapy, 3, 1010–1017, 1996).

It has in particular been demonstrated that compounds according to the invention in which the polyamines of the head group, which is bonded to the lipophilic radical $R_1$, have at least three nitrogen atoms, exhibit especially good properties; such compounds are accordingly especially preferred.

The present invention accordingly relates to new lipopolyamines of the general formula I, which are capable of transporting biologically active molecules into eukaryotic cells:

Formula I $$\left[H{-}(N{-}(CH_2)_a)_b \atop H\right]_{2-n} \quad N{-}(CH_2)_c{-}X{-}(CH_2)_d{-}N{-}R_1 \atop (H)_n \qquad (H)_m$$

$$\left[((CH_2)_e{-}N)_f{-}H \atop H\right]_{2-m}$$

and which, when a centre of asymmetry is present, occur in the D-, L- or DL-form, including salts thereof, wherein $R_1$ is a lipophilic radical of the following general formula:

$$R_1 = {-}(CH_2)_g{-}N{\diagup R_2 \atop \diagdown R_3}$$

in which $R_2$ and $R_3$ are each independently of each other dodecyl, dodecenyl, tetradecyl, tetradecenyl, hexadecyl, hexadecenyl, octadecyl, octadecenyl, or other alkyl radicals, which in all possible combinations may be saturated, unsaturated, branched, unbranched, fluorinated or non-fluorinated, and are constructed from 5, 6, 7, 8, 9, 10, 11, 12, 13, 14, 15, 16, 17, 18, 19, 20, 21, 22, 23, 24, 25, 26, 27, 28, 29 or 30 carbon atoms, and X is one of the following groupings:

$$X = \diagdown N{-}, \quad \diagdown N{-}(CH_2)_n{-}\overset{O}{\overset{\|}{C}}{-}NH{-},$$

$$\diagdown N{-}(CH_2)_r{-}\overset{O}{\overset{\|}{C}}{-}O{-}, \quad \diagdown N{-}(CH_2)_k{-}NH{-}\overset{O}{\overset{\|}{C}}{-},$$

-continued $$\diagdown N{-}(CH_2)_k{-}O{-}\overset{O}{\overset{\|}{C}}{-}, \quad \diagdown CH{-}\overset{O}{\overset{\|}{C}}{-}NH{-},$$

$$\diagdown CH{-}\overset{O}{\overset{\|}{C}}{-}O{-}, \quad \diagdown CH{-}\overset{O}{\overset{\|}{C}}{-}NH{-}(CH_2)_l{-}NH{-},$$

$$\diagdown CH{-}CH_2{-}NH{-}, \quad \text{or} \quad \diagdown CH{-}CH_2{-}O{-},$$

wherein m=0 and n=0, in which case g, may be 1,2,3,4,5,6,7 or 8, a may be 0,1,2,3,4,5 or 6, b may be 0,1,2,3,4,5 or 6, c may be 0,1,2,3,4,5 or 6, d may be 0,1,2,3,4,5 or 6, e may be 0,1,2,3,4,5 or 6, f may be 0,1,2,3,4,5 or 6, h may be 0,1,2,3,4,5 or 6, r may be 0,1,2,3,4,5 or 6 k may be 0,1,2,3,4,5 or 6 and l may be 0,1,2,3,4,5 or 6, or wherein m=0 and n=1, in which case g may be 1,2,3,4, 5,6,7 or 8, a may be 0,1,2,3,4,5 or 6, b may be 0,1,2,3,4,5 or 6, c may be 0,1,2,3,4,5 or 6, d may be 0,1,2,3,4,5 or 6, e may be 0,1,2,3,4,5 or 6, f may be 0,1,2,3,4,5 or 6, h may be 0,1,2,3,4,5 or 6, r may be 0,1,2,3,4,5 or 6, k may be 0,1,2,3,4,5 or 6 and l may be 0,1,2,3,4,5 or 6, or wherein m=0 and n=2, in which case g may be 1,2,3,4, 5,6,7 or 8, a may be 0,1,2,3,4,5 or 6, b may be 0,1,2,3,4,5 or 6, c may be 0,1,2,3,4,5 or 6, d may be 0,1,2,3,4,5 or 6, e may be 0,1,2,3,4,5 or 6, f may be 0,1,2,3,4,5 or 6, h may be 0,1,2,3,4,5 or 6, r may be 0,1,2,3,4,5 or 6, k may be 0,1,2,3,4,5 or 6 and l may be 0,1,2,3,4,5 or 6, or wherein m=1 and n=1, in which case g may be 1,2,3,4, 5,6,7 or 8, a may be 0,1,2,3,4,5 or 6, b may be 0,1,2,3,4,5 or 6, c may be 0,1,2,3,4,5 or 6, d may be 0,1,2,3,4,5 or 6, e may be 0,1,2,3,4,5 or 6, f may be 0,1,2,3,4,5 or 6, h may be 0,1,2,3,4,5 or 6, r may be 0,1,2,3,4,5 or 6, k may be 0,1,2,3,4,5 or 6 and l may be 0,1,2,3,4,5 or 6, or wherein m=1 and n=2, in which case g may be 1,2,3,4, 5,6,7 or 8, a may be 0,1,2,3,4,5 or 6, b may be 0,1,2,3,4,5 or 6, c may be 0,1,2,3,4,5 or 6, d may be 0,1,2,3,4,5 or 6, e may be 0,1,2,3,4,5 or 6, f may be 0,1,2,3,4,5 or 6, h may be 0,1,2,3,4,5 or 6, r may be 0,1,2,3,4,5 or 6, k may be 0,1,2,3,4,5 or 6 and l may be 0,1,2,3,4,5 or 6, or wherein m=2 and n=2, in which case g may be 1,2,3,4, 5,6,7 or 8, a may be 0,1,2,3,4,5 or 6, b may be 0,1,2,3,4,5 or 6, c may be 0,1,2,3,4,5 or 6, d may be 0,1,2,3,4,5 or 6, e may be 0,1,2,3,4,5 or 6, f may be 0,1,2,3,4,5 or 6, h may be 0,1,2,3,4,5 or 6, r may be 0,1,2,3,4,5 or 6, k may be 0,1,2,3,4,5 or 6 and l may be 0,1,2,3,4,5 or 6, and preferably a maximum of 50%, especially 30%, of the hydrogen atoms have been replaced by fluorine atoms.

Preferably, g>1. In preferred compounds c=3 and/or d=3. In especially preferred compounds a=0 or 3 and/or e=0 or 3 and/or b=0 or 1 and/or f=0 or 1.

Of particular interest are compounds and salts thereof having the following structures:
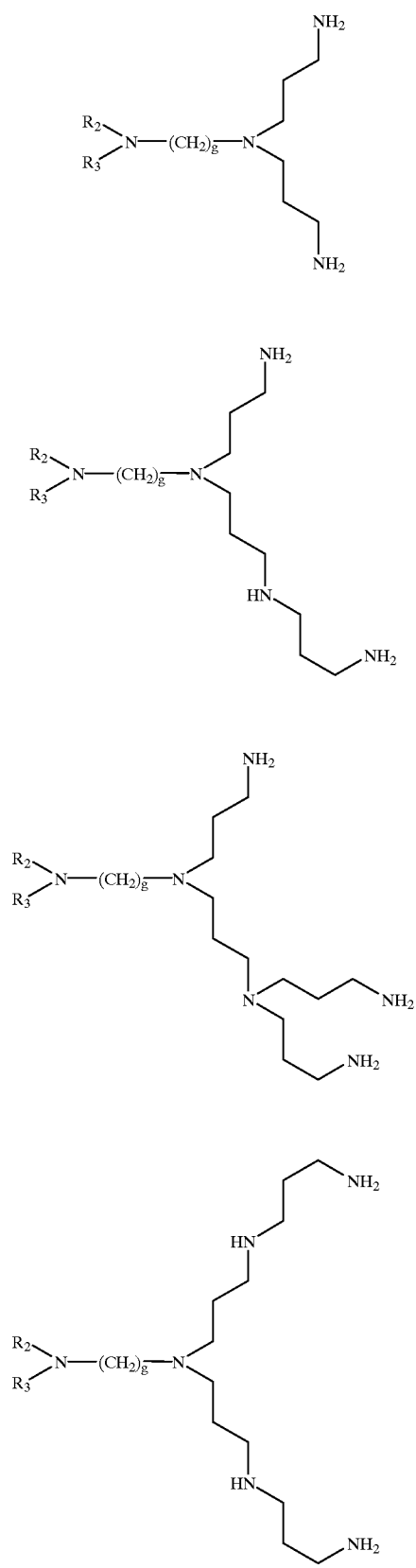
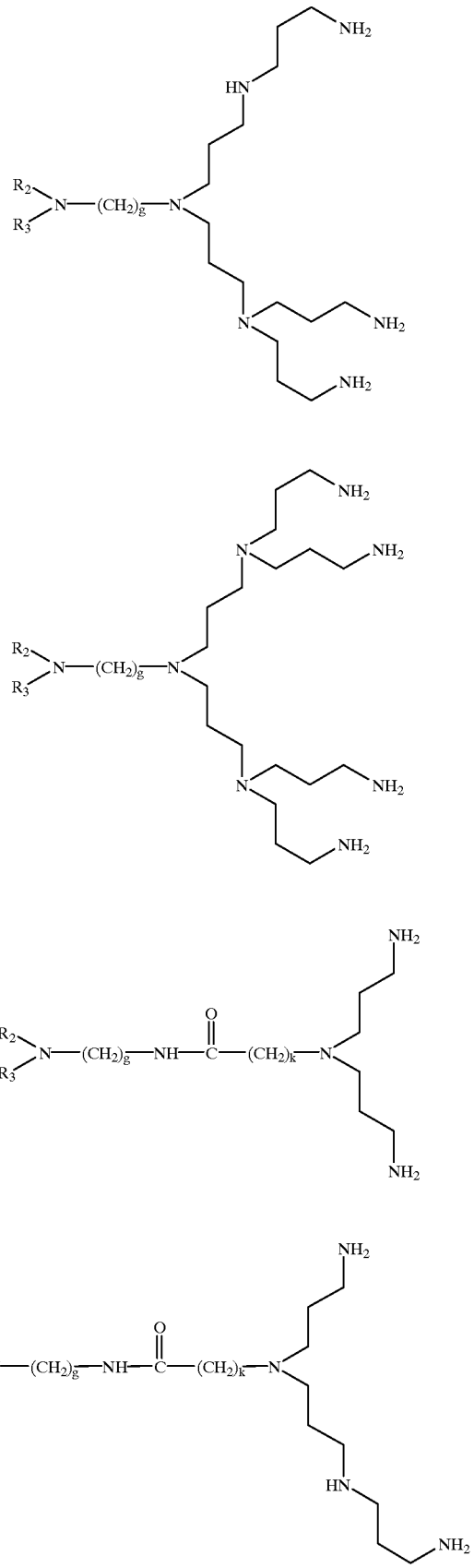

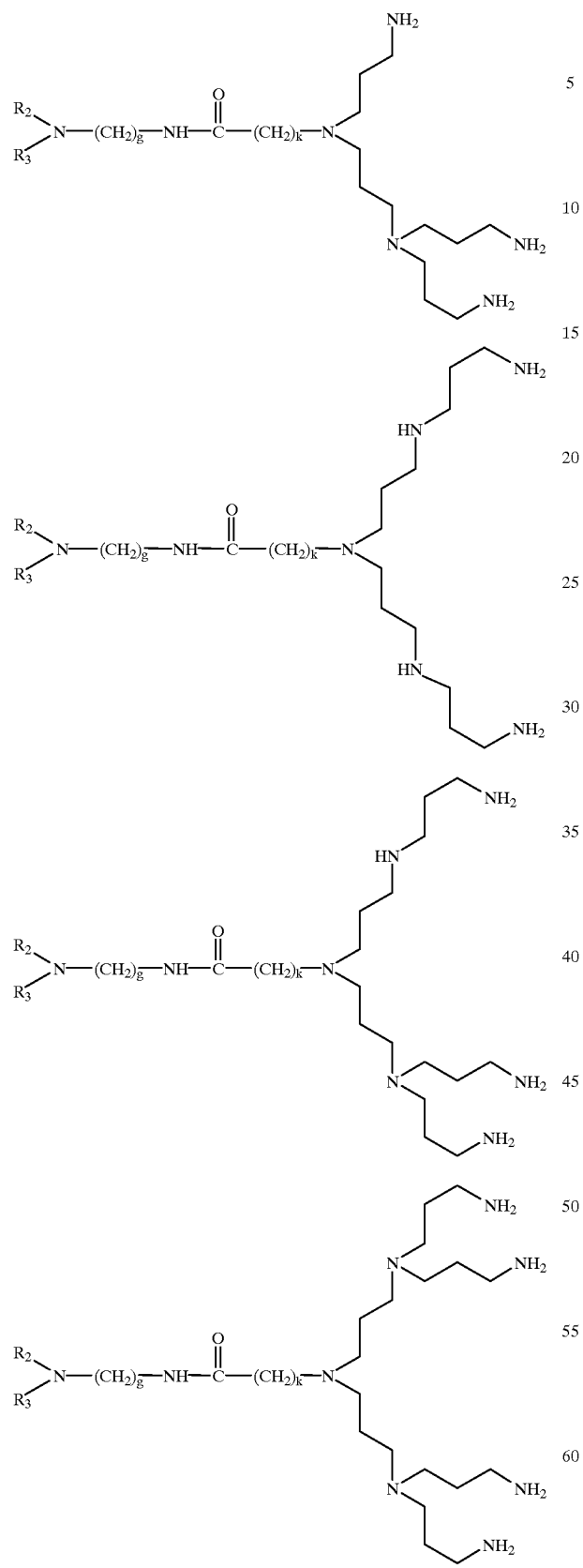
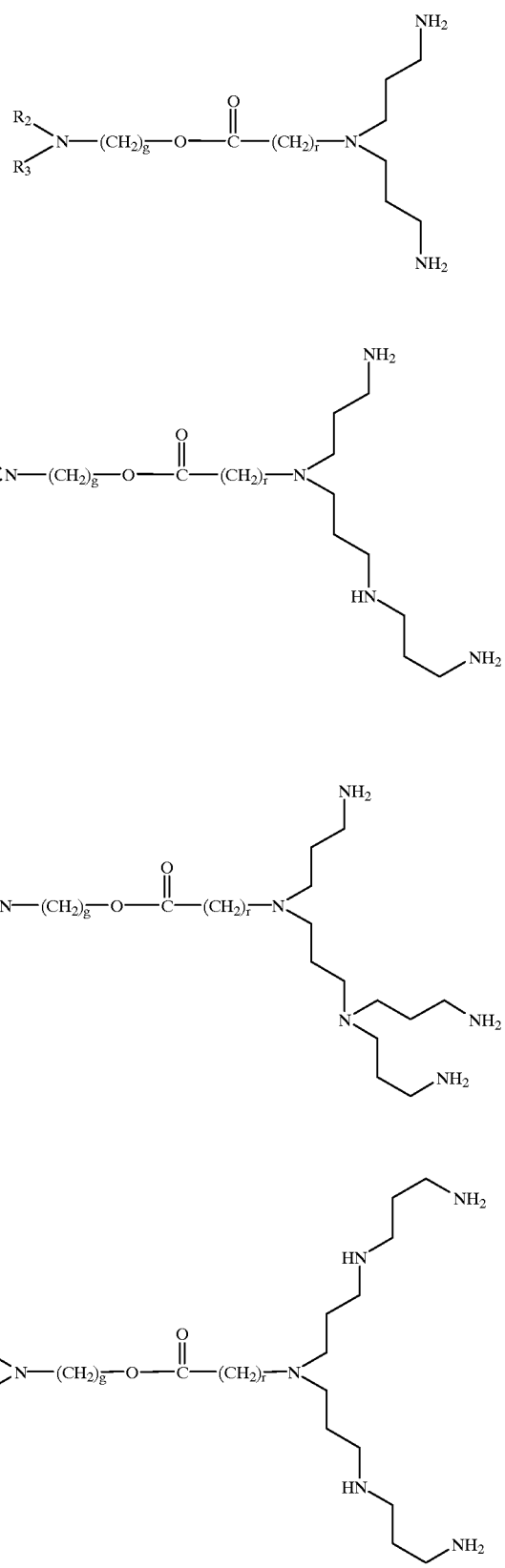

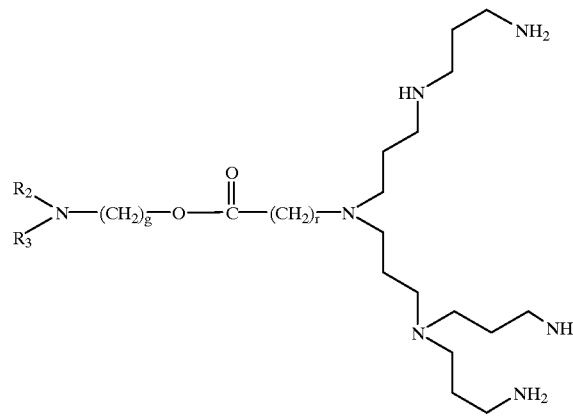
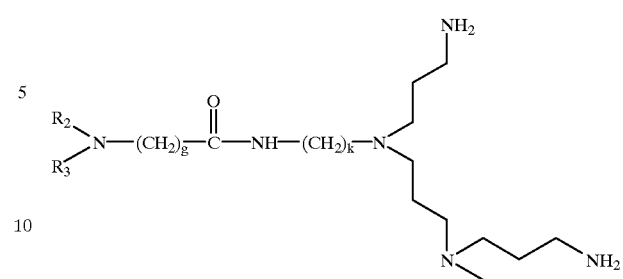
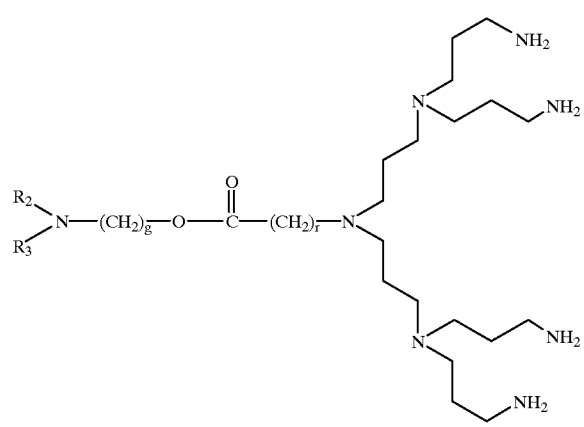
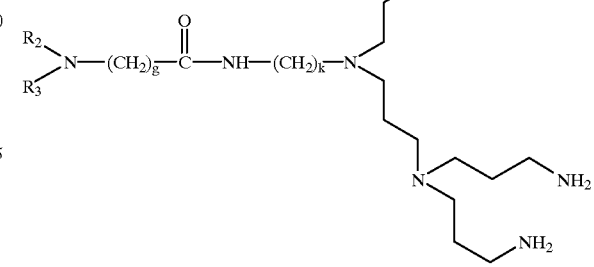
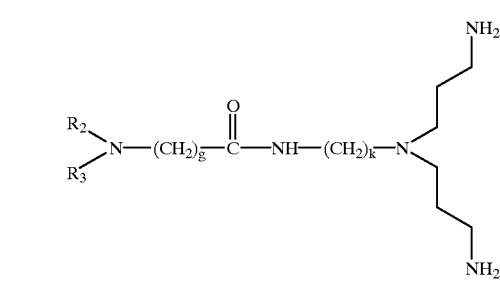
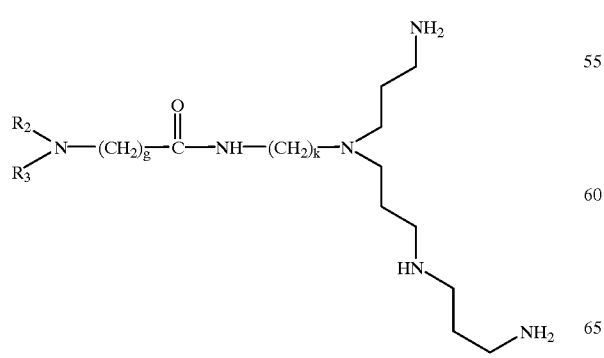
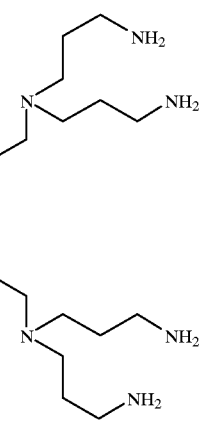

-continued
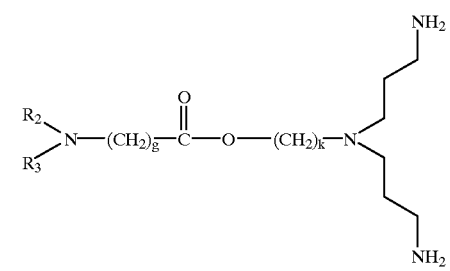
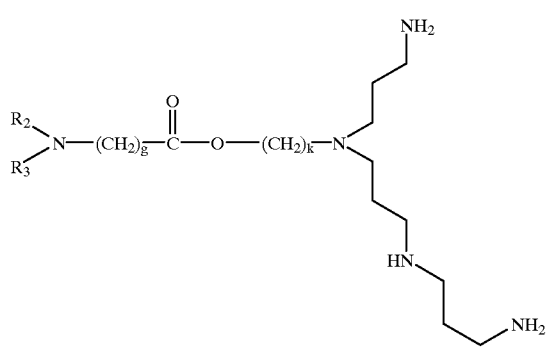
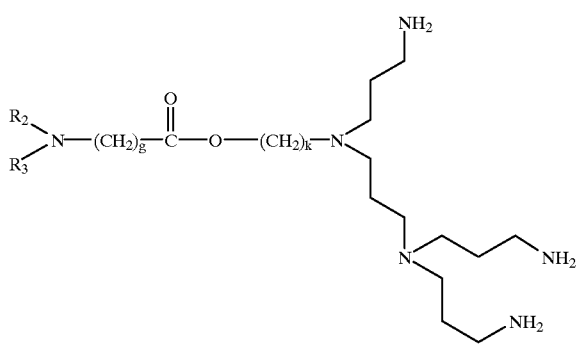
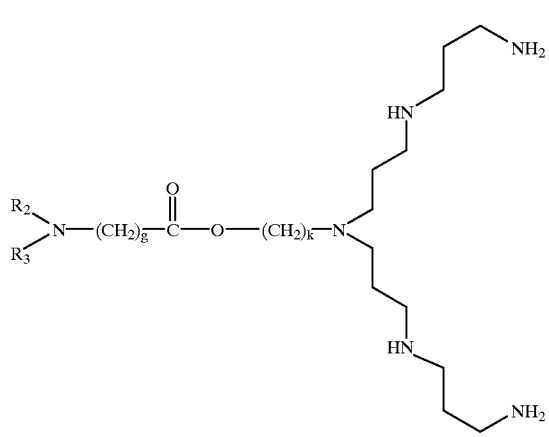
-continued
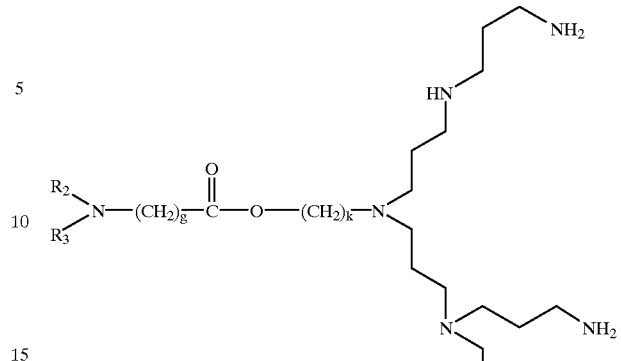
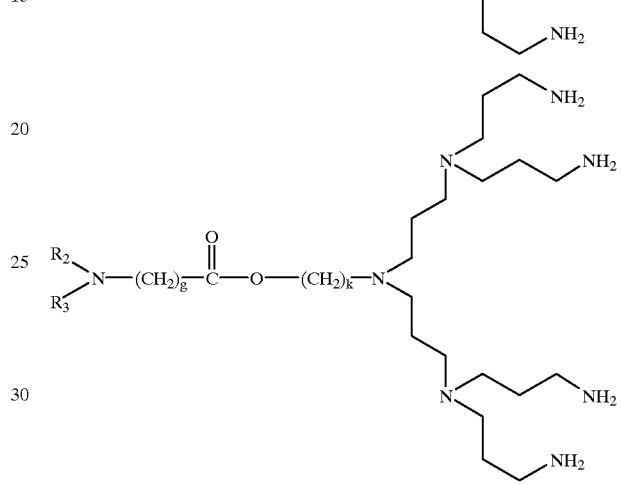
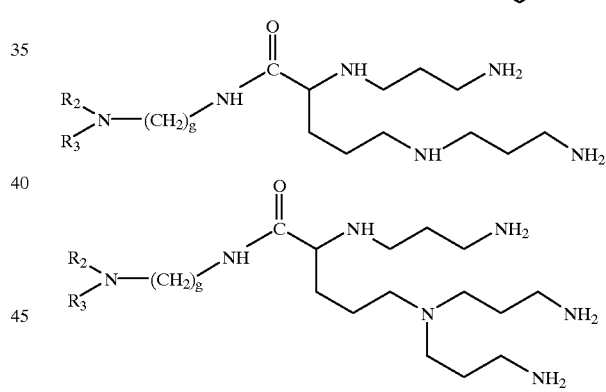
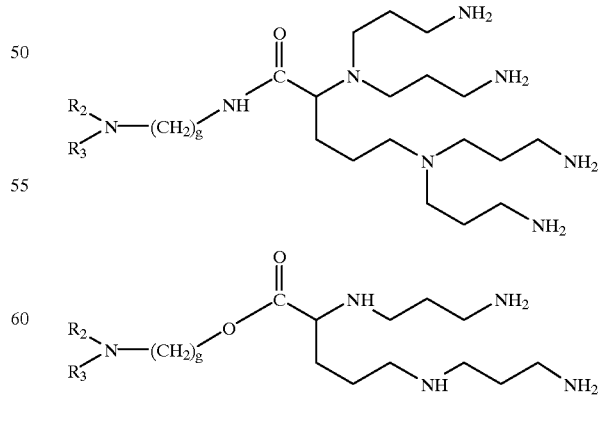

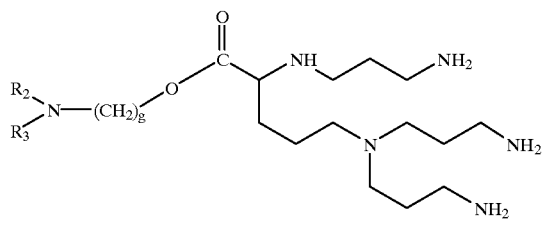
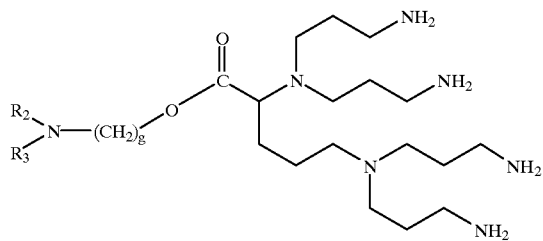
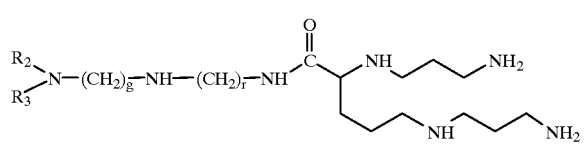
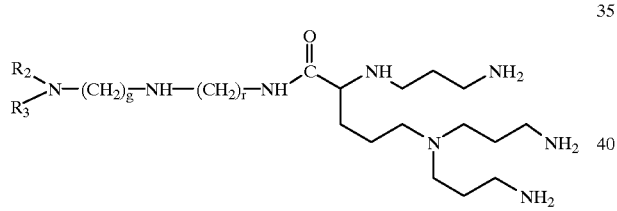
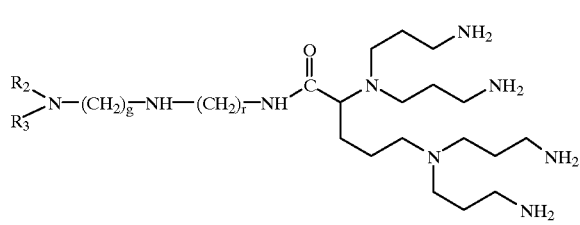
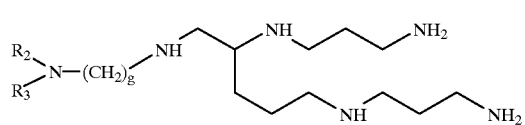
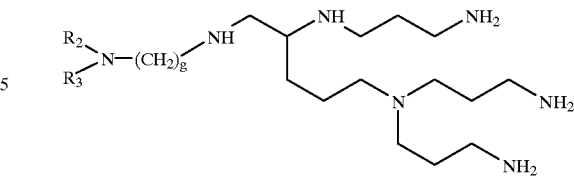
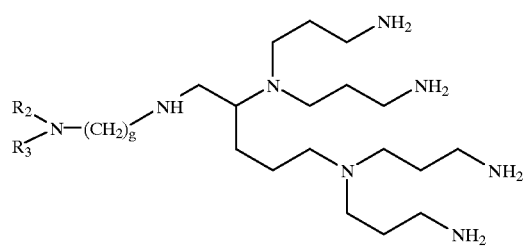
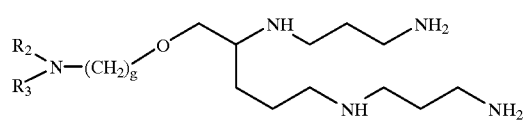
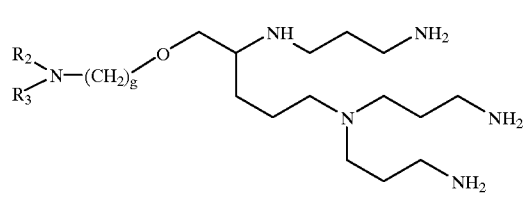
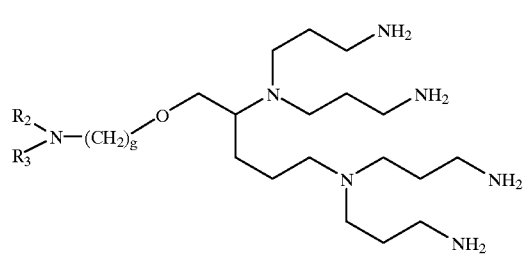
wherein h may be 0,1,2,3,4,5 or 6, r may be 0,1,2,3,4,5 or 6, k may be 0,1,2,3,4,5 or 6, 1 may be 0,1,2,3,4,5 or 6 and g may be 1,2,3,4,5,6,7 or 8, and $R_2$ and $R_3$, each independently of each other, may be dodecyl, dodecenyl, tetradecyl, tetradecenyl, hexadecyl, hexadecenyl, octadecyl or octadecenyl.
Among those, the following compounds and salts thereof are of more special interest:

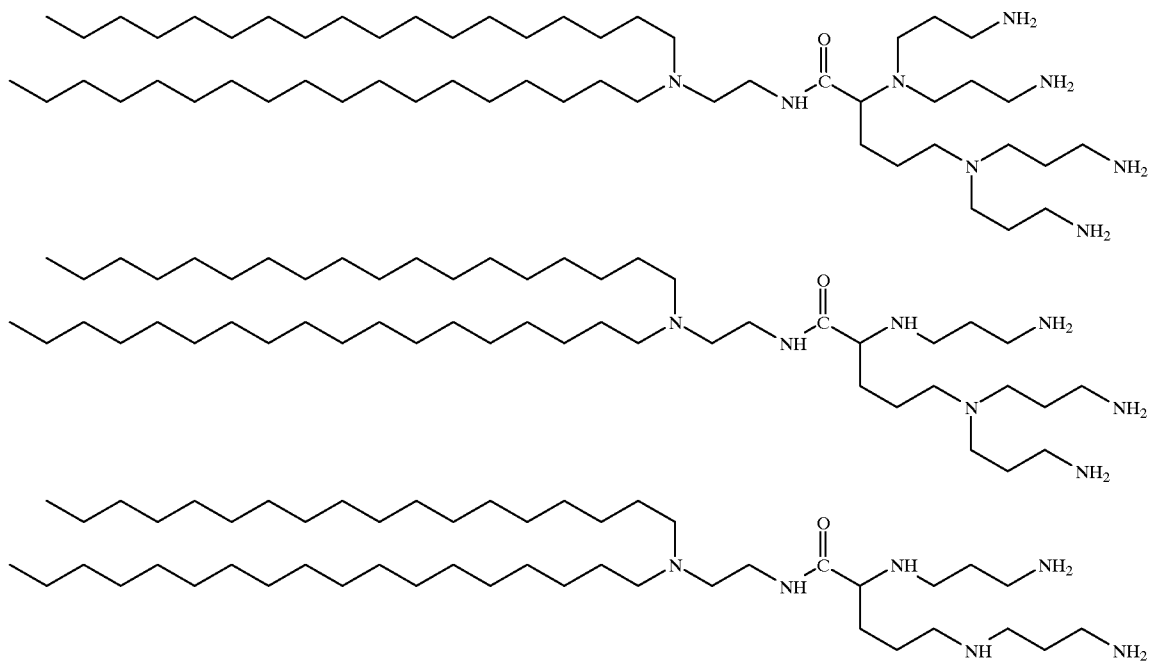

Of further special interest are compositions or formulations (which contain liposomes or micelles) that comprise at least one of the compounds according to the invention with or without colipids, such as, for example, dioleoyl phosphatidyl ethanolamine (DOPE), dioleoyl phosphatidyl choline, cholesterol or cholesteryl amine. The compositions or formulations (which contain liposomes or micelles) may comprise customary additives, carriers, adjuvants etc.

Of further special interest are methods of introducing biologically active compounds, such as DNA, RNA, ribozymes, antisense DNA, PNA, peptides, peptoids and proteins into eukaryotic cells, in which the compounds, compositions or formulations according to the invention are complexed with the (biologically active) compounds to be introduced, and the resulting complexes are brought into contact with eukaryotic cells in vivo or in vitro.

Of further special interest is the use of the compounds, compositions or formulations (for the preparation of a medicament or a reagent) according to the invention for the in vivo or in vitro introduction of biologically active compounds, such as DNA, RNA, ribozymes, antisense DNA, PNA, peptides, peptoids and proteins, into eukaryotic cells.

Of further special interest is the use of the compounds, compositions or formulations (for the preparation of a medicament or a reagent) according to the invention for the in vivo or in vitro introduction of biologically active compounds, such as DNA, RNA, ribozymes, antisense DNA, PNA, peptides, peptoids and proteins, into eukaryotic cells in combination with so-called "enhancers", which increase the action of the compounds according to the invention.

The lipids according to the invention thus contain polyamines as head groups having DNA affinity, which are bound to a specific lipophilic radical, where appropriate by way of a spacer.

The lipids according to the invention are especially valuable in view of their stability in solution and their simultaneous low toxicity for the cell, combined with extraordinarily good transfection properties.

It has thus been possible to demonstrate that, compared with Lipofectamin™ (Gibco-BRL: Life Technologies Inc.), the most effective transfection reagent from the group of the lipopolyamines known to date in this specialised field, the compounds according to the invention exhibit better transfection properties when carrying the same head group. Not only is the transfection efficiency greater in both serum-free and serum-containing media, but it has also been shown that a high level of transfection efficiency can be achieved over a substantially broader DNA/lipid ratio.

The compounds according to the invention can be prepared by reacting one amino group of a diamine with an alkylation reagent, optionally in the presence of a base, and coupling the other amino group with an optionally BOC-protected carboxypolyalkylamine. The other amino group is preferably protected in the first reaction step, for example with a BOC group, which is removed before reaction with the carboxypolyalkylamine. An alkyl bromide, such stearyl bromide, may be used as alkylation reagent and, for example, triethylamine or 4-methyl-morpholine may be used as base.

In the following, a corresponding synthesis is explained in the example of one of the more especially valuable compounds, namely N-[2,5-bis[(3-aminopropyl)amino]-1-oxopentyl]-N',N'-dioctadecylethylenediamine.

This method uses as starting material alkylenediamine in which one amino group has been protected with N-tert-butoxycarbonyl (BOC-protected). The free amino group is derivatised by alkyl bromides, such as, for example, stearyl bromide, in the presence of a base. The protected amino function is then deprotected in a manner customary per se, and coupled in a manner customary per se to carboxypolyalkylamine BOC-protected at all (reactive) amino functions (in this case BOC-protected carboxyspermine). After deprotecting that head group, which is carried out in a manner customary per se, the desired compounds are obtained in the form of free amines or in the form of salts, according to the working up.

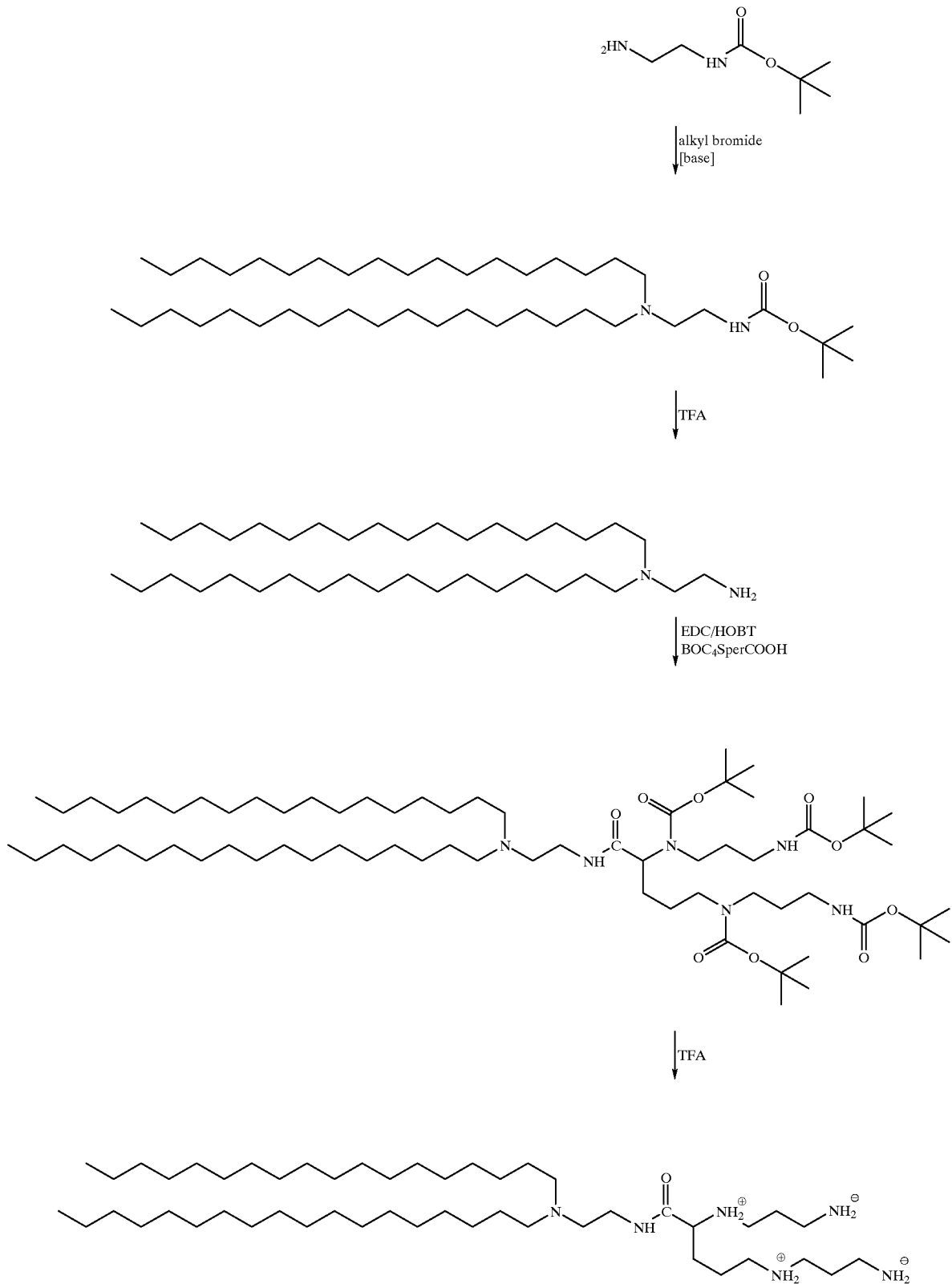

In a further embodiment, a diamine optionally protected at one amino group is reacted with acrylonitrile and the product is reacted with an alkylation reagent, such as stearyl bromide, optionally in the presence of a base. The product may then be hydrogenated.

A further preferred compound, namely N,N-bis(3-aminopropyl)-N',N'-dioctadecylethylene-diamine, can be prepared in that manner. It is obtained using N-tert-butoxycarbonylethylene-diamine (BOC-ethylenediamine) as starting material, by reaction with acrylonitrile, alkylation with alkyl bromide and subsequent hydrogenation. The subsequent steps are used for working up.

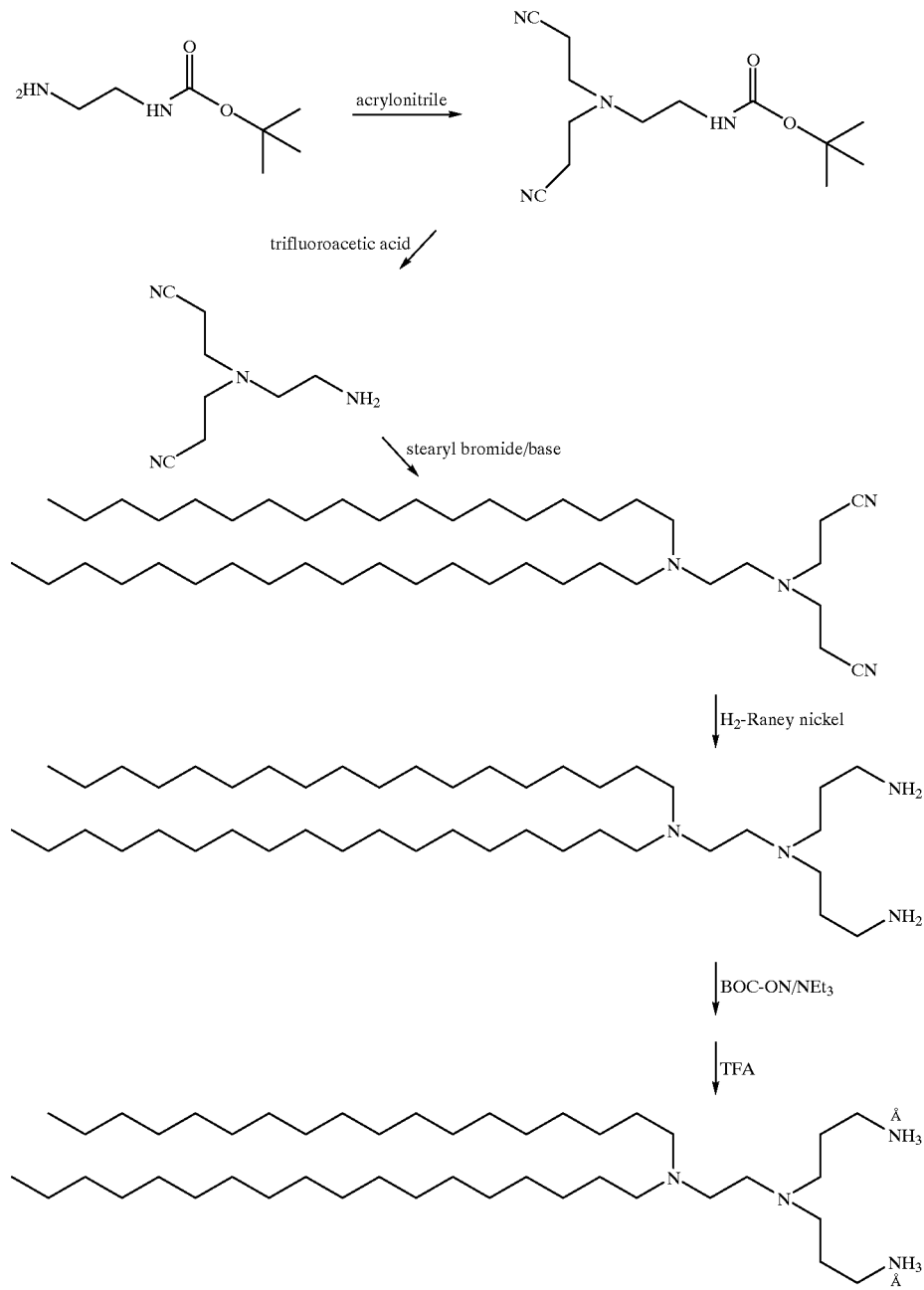

An alternative route to the same molecule is the alkylation of N,N-dioctadecylethylenediamine with N-BOC-3-bromopropylamine:

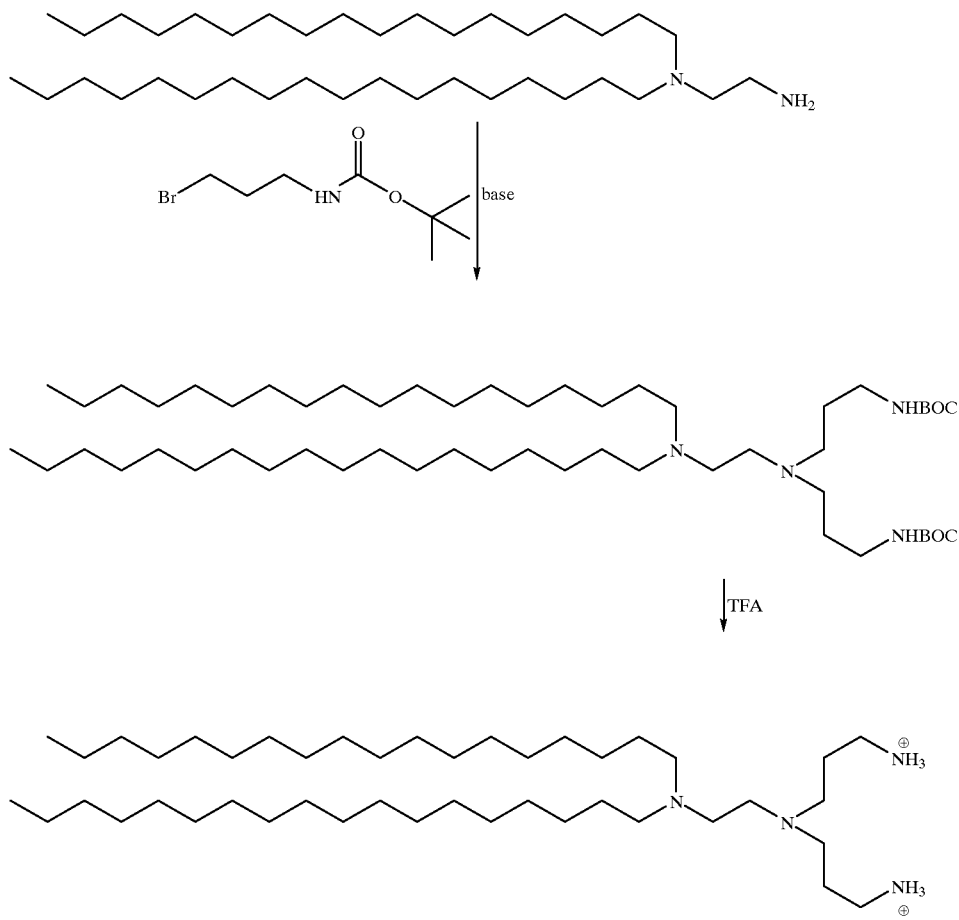

By the selection of suitable conditions known per se to the person skilled in the art, such as temperature, time, stoichiometric ratio, etc., the polyamine head groups can be lengthened, or also branched polyamine head groups can be produced. It is possible to produce the head group individually and then couple it to the lipophilic radical, or to extend on the molecule head groups that have already been coupled. For example, it is possible to proceed according to the following reaction scheme, which is known per se and which moreover is also contained in the previous Example:

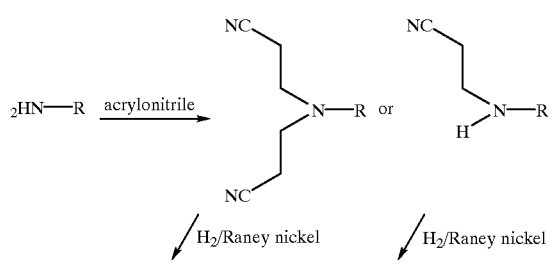

-continued

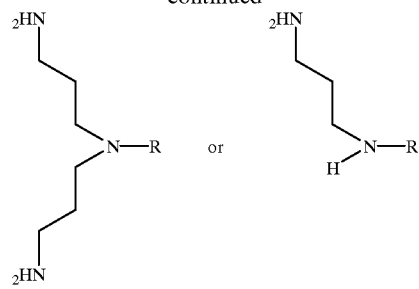

The reaction of ornithine with acrylonitrile may be given as an explicit example. By means of the amount of acrylonitrile and the correct choice of reaction temperature, it is possible for the desired product to be obtained as the major product. The hydrogenation of the nitriles to the amines and their protection by the BOC protecting group are carried out according to J. P. Behr et al, Proc. Natl. Acad. Sci., USA, 86, pp. 6982–6986, 1989 analogously to the synthesis of tetra-BOC-carboxyspermine.

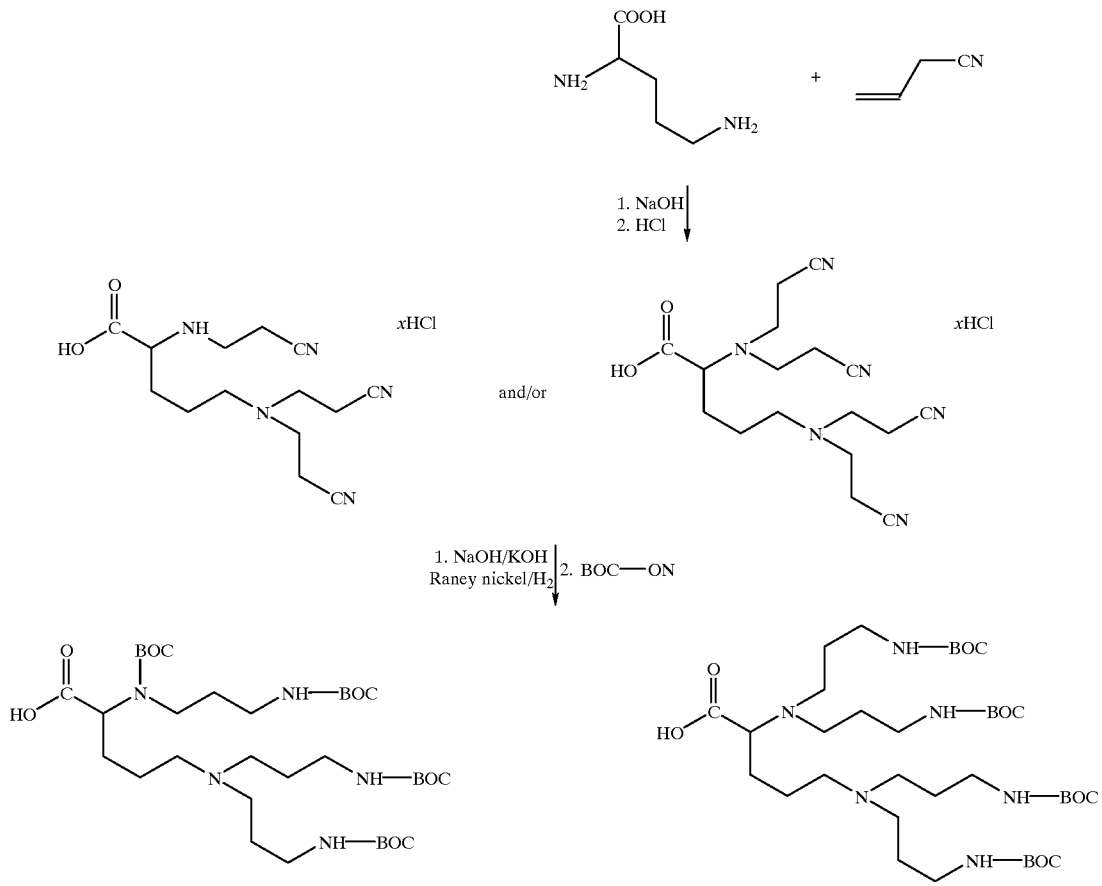

A further possible method of lengthening and branching the polyamine head groups comprises the alkylation of amines by N-(tert-butoxycarbonyl)-3-bromopropylamine:

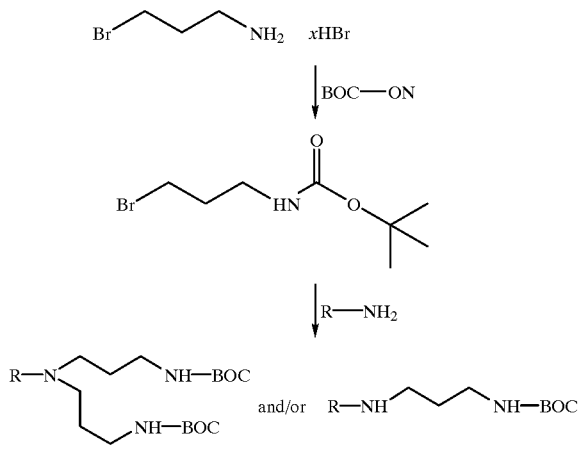

Generally, all of the lipids mentioned can be produced using the methods stated in the Examples hereinbelow and hereinafter (protection and deprotection of amino functions with the BOC protecting group, alkylation of amino functions with alkyl bromides, linkage of amide bonds analogously to known peptide chemistry, cyanoethylation of amino functions via acrylonitrile, hydrogenation of cyano functions to amines) or using methods generally known and trusted by the organic chemist (alkylation of alcohols, linkage of ester bonds, reduction of esters to ethers and of amides to amines via lithium alanate).

With regard to the preparation of the compounds that contain the two last-described spacers, reference is made to WO 98/02191. A description is given in that specification as to how esters and amides can be reduced to ethers and amines by lithium alanate, without attacking the BOC protecting group. Using that method, such compounds are obtained from the corresponding precursors.

The compounds according to the invention may be used per se in aqueous solution or aqueous buffer solution or ethanolic solution. It is also possible, however, for liposomes (or micelles) to be formulated with the above-mentioned lipids alone, or in combination with other lipids, such as, for example, cholesterol, cholesteryl amine, dioleoyl phosphatidyl ethanolamine (DOPE) or dioleoyl phosphatidyl choline (DOPC).

In order to increase the transfection efficiency of the lipids according to the invention, it is possible to transfect cells in the presence of substances that inhibit the enzymatic activity in the lysosomes, so-called lysosomatotropic substances, such as, for example, chloroquine or proteins having lysosomatropic activity that are derived from viruses.

It is also possible to use so-called enhancers in combination with the cationic lipids. Enhancers increase the action of the cationic lipids. There are those enhancers that have no transfecting properties themselves and those that can be used for transfection even without cationic lipids. In the case of the former the result is a simple increase (amplification) of the transfection efficiency of the cationic lipids. In the case of the latter, in combined use the transfection efficiency demonstrated is greater than in the case of individual use. The combined action accordingly occurs as a result of a synergy effect. Enhancers display their activity as a rule by a precondensation of the DNA to be transfected, or they increase the propensity to be permeated of the cell membrane that is to be penetrated. Examples of enhancers include polyethyleneimine, transferrin, protamine sulphate, polyhistone, fusogenic peptides, virus coats, viral surface peptides, replication-deficient viruses etc.

The lipopolyamines according to the invention are positively charged at physiological pH and are accordingly able to form stable aggregates with negatively charged macromolecules, especially with DNA and related substance classes. The macromolecules coated with the lipopolyamines and rendered positively charged interact with the negatively charged cell membrane in a manner that results in the introduction of the macromolecules into the cell. With this process both in vitro and in vivo applications are possible.

Compared with specifically targeted receptor-mediated endocytosis (Wu et al., J. Chem. 262, 4429–4432, 1987), in which polycations, which are also referred to as DNA binders (for example polylysine etc.), are bound to so-called internalisation factors (for example certain glycoproteins) which bind in a specifically targeted manner to surface receptors of certain cells, the lipids according to the invention, and liposome formulations thereof, do not exhibit cell specificity. A specifically targeted delivery by the lipids according to the invention or liposome formulations thereof can be achieved by the charges of lipids and of the biomolecules to be transported being neutralised and, in addition, internalisation factors being attached to the aggregate between biomolecule and lipids. This can be accomplished, for example, by liposome formulation with colipids where the colipids carry such internalisation factors as head group.

Another possibility is an aggregate of biomolecule, lipids and internalisation factors that is formulated to a neutral charge. So-called internalisation factors are transferrin, galactose, mannose, mannose-6-phosphate, asialglycoprotein, conalbumin, lectins, transcobalamine, α-2-macroglobulin, biotin, folate, mannosylated glycoproteins. Further examples may be found in EP 0 535 756, EP 0 544 292, WO 94/21808, which are incorporated herein by reference.

In an analogous manner to internalisation factors, it is also possible to use cell-specific antibodies.

The compounds according to the invention may be used for therapeutic purposes. In particular, such compounds may be used for the gene therapy of, for example, cystic fibrosis, muscular dystrophy, phenylketonuria, maple syrup disease, propionazidaemia, methylmalonazidaemia, adenosine deaminase deficiency, hypercholesterolaemia, haemophilia and β-thalassaemia. Gene therapy treatment methods are also of interest when hormones, growth factors, cytotoxins or proteins having an immunomodulating effect are to be synthesised in the organism. For the above-mentioned purposes, DNA fragments can be introduced by means of these lipids into cells in which that DNA exhibits the desired activity. The desired activity may be the replacement in the diseased cell type of missing or defective DNA regions or the inhibition in the diseased cell type of DNA regions (for example antisense DNA/RNA) that trigger the disease. In that manner tumour-suppressing genes may be used in cancer therapy, or assistance in the prophylaxis of coronary and vascular diseases may be afforded by the introduction of cholesterol-regulating genes. In addition, DNA that encodes ribozymes, or ribozymes themselves, may be introduced into diseased cells. The translation of that DNA generates active ribozymes, which catalytically cleave mRNA at specific sites and in that manner prevent transcription. In that way, for example, viral mRNA can be specifically cleaved without affecting a different cellular mRNA. The replication cycle of viruses (e.g. HIV, herpes, hepatitis) can be interrupted in that way.

Transfection also plays an ever increasing role in cancer therapy in the preparation of cancer vaccines. That field is accordingly also a possible field of use for the compounds according to the invention.

A further use for such lipids may be, for example, in inoculation processes that function on the basis of the expression of DNA that encodes immunogenic peptides in the human and animal body. For that purpose lipid/DNA complexes are used as inoculation substances. The introduction of the DNA into the body cells results in the expression of the immunogenic peptide and thus triggers the immune response.

Apart from DNA, it is also possible for other macromolecules, such as, for example, PNA, peptides, peptoids or proteins, to be introduced into cells. For that purpose the macro-molecules may be coated with the lipopolyamines according to the invention per se, or may be incorporated in liposomes that comprise as components the lipopolyamines according to the invention, or may be adsorbed on the surface thereof, if a negative net charge exists. By bringing such aggregates into contact with cells, transport of those molecules through the cell wall occurs. Therapeutic peptides have a favourable effect on numerous diseases. Such peptides or proteins include, for example, lymphokines, interleukins, tumour necrosis factors or interferons, also growth factors, tissue plasminogen activator, factor VIII:c, granulocyte-macrophage colony-stimulating factor, erythropoietin, insulin, calcitonin, thymidine kinase and others. In addition toxic peptides, such as ricin, diphtheria toxin and others, may be used therapeutically with success in that way. Peptoids may also be used successfully as peptide analogues to prevent a rapid enzymatic degradation in the body.

Owing to their positive charge, the lipids according to the invention are used predominantly to complex negatively charged molecules, in view of the negative charge thereof, and to introduce them into cells. By so-called "self assembling systems", however, it is also possible for positively charged molecules to be transported, by first complexing negatively charged liposomes with those positively charged molecules. By so selecting the ratios that a negative net charge remains, those complexes can be rendered positively charged with the lipo-polyamines according to the invention, per se or in the form of liposomes, by bringing into contact the oppositely charged components. The resulting positively charged complete complexes are taken up by the cells.

Further possible uses for cationic lipids may be found in the publications WO 90/11092, WO 91/16024, WO 93/03768, Science 258, 744–746, 1992, which are included herein by reference.

Examples of sequences of genetic material currently considered to be therapeutically promising may be found in the review by F. W. Anderson, Science 256, 808, 1992, which are also included herein by reference.

EXAMPLES

REFERENCE SOURCES

1. Plasmids: pCMV<Sport>β-Gal; Gibco BRL, Life Technologies
2. β-Galactosidase Assay Kit, Stratagene
3. Tetra-BOC-carboxyspermine was synthesised according to J.-P. Behr et al. Proc. Natl. Acad. Sci., USA, 86, pp. 6982–6986, (1989).
4. Lipofectamin™; Gibco-BRL: Life Technologies Inc.
5. N-tert-butoxycarbonylethylenediamine, Aldrich.
6. O-(tert-butoxycarbonyl)-phenylglyoxylic acid nitrile oxime (BOC-ON); Aldrich.
7. N'-(3-dimethylaminopropyl)-N-ethylcarbodiimide methiodide (EDC), Aldrich.
8. 1-Hydroxy-1H-benzotriazole (HOBT), Aldrich.
9. 4-Methylmorpholine, diisopropylethylamine (DIPEA), triethylamine, Aldrich.
10. Trifluoroacetic acid (TFA), Aldrich.
11. Dulbecco's modified Eagle's Medium (DMEM), Gibco-BRL: Life Technologies Inc.
12. Foetal calf serum (FCS), Biochrom.
13. Penicillin, streptomycin, SIGMA.

Example 1
Transfection Reagent 1
Synthesis of N-tert-butoxycarbonyl-N',N'-dioctadecylethylenediamine 646 mg (1.94 mmol, MW 333.4) of octadecyl bromide, 135 mg (0.84 mmol, MW 160.22) of N-tert-butoxycarbonylethylenediamine (BOC-ethylenediamine) and 332 μl (1.94 mmol, MW 129.25, d 0.755) of diisopropylethylamine (DIPEA) are dissolved in 10 ml of acetonitrile and boiled under reflux overnight. After the addition of 100 ml of ether the whole is washed with water. The organic phase is dried with magnesium sulphate and the solvent is removed. The already relatively pure product is purified by flash chromatography.

$C_{43}H_{88}O_2N_2$
MW 664.12
$R_f$=0.44(9:1 v/v chloroform/methanol)
MS (FAB): 665.7 (M+1)
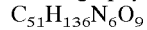 NMR (CDCl$_3$): 0.88 (tr, 6H, CH$_3$); 1.26 ("s", 60H, CH$_2$); 1.40 (m, 4H, N—CH$_2$C$\underline{H}_2$); 1.44 (s, 9H, CH$_{3BOC}$); 2.40 (tr, 4H, N—CH$_2$); 2.50 (tr, 2H, N—CH$_2$); 3.15 (m, 2H, OCO—N—CH$_2$).
$^{13}$C NMR (CDCl$_3$): 13.1 (CH$_3$); 22.7, 27.0, 25.5 (CH$_2$); 28.5 (CH$_{3BOC}$); 29.4, 29.6, 29.7, 29.7 (CH$_2$); 53.2 (N—CH$_2$); 54.0 (N—CH$_2$); 78.9 (C$_{qBOC}$); 156.1 (OCO).
Yield: 390 mg (69%)

Synthesis of N-[tetra-tert-butoxycarbonyl-[(2.5-bis(3-aminopropyl)amino)-1-oxopentyl]]N',N'-dioctadecylethylenediamine 157 mg (0.236 mmol, MW 665.12) of N-tert-butoxycarbonyl-N',N'-dioctadecylethylenediamine are taken up in 4 ml of a 1:3 v/v mixture of trifluoroacetic acid (TFA) and methylene chloride. After 2 to 3 hours, the mixture is subject to rotary evaporation and dried for 0.5 h under a high vacuum. The product is then taken up in 6 ml of a 1:1 v/v mixture of DMF and methylene chloride, and 300 μl of 4-methylmorpholine are added. 152.6 mg (0.236 mmol, MW 646.8) of tetra-BOC-carboxyspermine are then dissolved in 2 ml of a 1:1 v/v mixture of dimethylformamide (DMF) and methylene chloride and added thereto. In addition, 45 mg (0.330 mmol) of 1-hydroxy-1H-benzotriazole (HOBT) and 98 mg (0.330 mmol) of N'-(3-dimethylaminopropyl)-N-ethylcarbodiimide methiodide (EDC) are added and the whole is stirred at room temperature for 50 hours. The solvent is removed by rotary evaporation and the residue is taken up in methylene chloride and washed with water. The organic phase is dried with sodium sulphate and subject to rotary evaporation. The crude product is purified by flash chromatography.

$C_{51}H_{136}N_6O_9$
MW 977.65
$R_f$=0.40 (9:1 v/v methylene chloride/methanol)
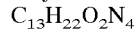 NMR (CDCl$_3$): 0.88 (tr, 6H, CH$_3$); 1.25 ("s", 64H, CH$_2$); 1.44 (m, 36H, CH$_{3BOC}$); 1.67 (m, 8H, spermine: CH$_2$C$\underline{H}_2$CH$_2$); 2.36 (mr, 4H, stearyl: N—CH$_2$); 2.51 (m, 2H, ethylenediamine: N—CH$_2$); 3.1–3.25(m, 10H, OC—N—CH$_2$).
Yield: 135 mg (59%)

Synthesis of N-[2.5-bis((3-aminopropyl)amino)-1-oxopentyl]-N',N'-dioctadecylethylenediamine (TFA Salt)

70 mg of N-[tetra-tert-butoxycarbonyl-[(2,5-bis(3-aminopropyl)amino)-1-oxopentyl]]-N',N'-dioctadecylethylenediamine are dissolved in 2 ml of a mixture of methylene chloride and trifluoroacetic acid (3:1 v/v) and stirred for 1.5 hours at RT. The mixture is then subject to rotary evaporation, taken up in 10 ml of a mixture of water/tert-butanol (1:1 v/v) and lyophilised.

$C_{53}H_{104}ON_6$(.4 CF$_3$COOH)
MW 793.52 (+4×114=1249.52)
Yield: 100%

Example 2
Transfection Reagent 2
Synthesis of N',N'-bis(2-cyanoethyl)-N-tert-butoxycarbonylethylenediamine 500 mg (3.12 mmol, MW 160.22) of N-tert-butoxycarbonylethylenediamine are dissolved in 5 ml of water and 0.65 ml (9.8 mmol, MW 53.06) of acrylonitrile is added. The whole is then stirred at room temperature for 7 days. The mixture is then covered with a layer of ethyl acetate and extracted by shaking and the organic phase is separated off. After drying over sodium sulphate the residue is subject to rotary evaporation.

$C_{13}H_{22}O_2N_4$
MW 266.34
$R_f$=0.69 (9:1 v/v chloroform/ethanol)
Yield: 660 mg (80%)

Synthesis of N',N'-bis(2-cyanoethyl)-N',N'-dioctadecylethylenediamine 660 mg (2.48 mmol, MW 266.34) of N',N'-bis(2-cyanoethyl)-N-tert-butoxycarbonylethylenediamine are taken up in 10 ml of a 1:3 v/v mixture of trifluoroacetic acid and methylene chloride. After 2 to 3 hours, the mixture is subject to rotary evaporation and dried for 0.5 hours under a high vacuum. The residue is subsequently lyophilised from butanol/water (1:1 v/v). The resulting trifluoroacetate is dissolved in 40 ml of dry acetonitrile together with 2.43 g (7.28 mmol, MW 333.4) of octadecyl bromide and 2.23 ml (1.68 g, 13.02 ml, MW 129.25, d 0.755) of diisopropylethylamine (DIPEA), and boiled under reflux for 24 hours. The crude product is purified by flash chromatography.

$C_{44}H_{86}N_4$
MW 671.16
$R_f$=0.42 (9:1 v/v methylene chloride/methanol)
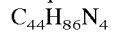 NMR (CDCl$_3$): 0.88 (tr, 6H, CH$_3$); 1.26 ("s", 60H, CH$_2$); 1.42 (m, 4H, N—CH$_2$C$\underline{H}_2$); 2.42 (m, 4H, N—CH$_2$); 2.48 (tr, 4H, CH$_2$—CN); 2.50 (m, 2H, N—CH$_2$); 2.50 (m, 2H, N—CH$_2$); 2.92 (tr, 4H, N—CH$_2$).
Yield: 330 mg (20%)

Synthesis of N',N'-bis(3-aminopropyl)-N,N-dioctadecylethylenediamine (TFA Salt)

2.5 g of Raney nickel are added to 50 ml of water. With stirring, 4.5 g of sodium hydroxide are added so rapidly thereto that the water does not quite boil over, and the whole is then stirred for half an hour. 320 mg (0.48 mmol, MW 671.2) of N',N'-bis(2-cyanoethyl)-N,N-dioctadecylethylenediamine are taken up in 500 ml of 0.5M potassium hydroxide solution (in EtOH/water 95:5 v/v). The activated Raney nickel is separated from the supernatant by decanting and is added to the starting solution. The whole is then hydrogenated for 24 hours using a hydrogenation plant. After removing the solvent by rotary evaporation, the residue is dissolved in 5 ml of methylene chloride. 500 mg (2.02 mmol, MW 246.27) of O-(tert-butoxycarbonyl)-phenylglyoxylic acid nilrile oxime (BOC-ON) are added thereto and the whole is stirred at room temperature for 24 hours. Subsequently, concentration by rotary evaporation is carried out. The crude product is purified by flash chromatography. The product is then taken up in 10 ml of a 1:3 v/v mixture of trifluoroacetic acid and methylene chloride. After 2 to 3 hours, the whole is subject to rotary evaporation and dried for 0.5 hours under a high vacuum. Finally, lyophilisation from butanol/water (1:1 v/v) is carried out $C_{44}H_{94}N_4 \cdot 4\ CF_3COOH$
MW 679.21 (+4×114=1135.21)
MS (ESI): 680.2
Yield: 250 mg (58% based on nitrile)

Example 3
Branched Head Groups
Synthesis of N-(tert-butoxycarbonyl)-3-bromopropylamine 500 mg (2.28 mmol; MW 218.94) of 3-bromo-1-propylamine hydrobromide (Aldrich) are dissolved together with 1.13 g (4.59 mmol; MW 246.27) of O-(tert-butoxycarbonyl)phenylglyoxylic acid nitrile oxime (BOC-ON) and 0.65 ml (0.46 g; 4.6 mmol) of triethylamine in a mixture of acetone and water (1:1, v/v). After stirring for 2 hours, the whole is concentrated and taken up in methylene chloride. The organic phase is washed with water, dried with sodium sulphate and concentrated by rotary evaporation. The crude product is purified by flash chromatography.

$C_8H_{16}O_2NBr$
MW 238.31
$R_f$=0.84 (9:1 v/v methylene chloride/methanol)
$^1H$ NMR (CDCl$_3$): 1.36 (br s, 9H, CH$_{3BOC}$); 1.98 (m, 2H, C—CH$_2$—C); 3.19 (m, 2 H, Br—C$\underline{H}_2$); 3.38 (m, 2H, N—CH$_2$); 4.90 (br s, 1H, N—H).
$^{13}C$ NMR (CDCl$_3$): 28.2 (CH$_3$); 30.6, 32.6, 38.8 (CH$_2$); 79.1 (C$_q$); 155.8 (C=O).
Yield: 250 mg (46%)

Synthesis of N',N'-bis(3-aminopropyl)-N,N-dioctadecylethylenediamine (TFA Salt)

200 mg (0.3 mmol, MW 665.12) of N-tert-butoxycarbonyl-N',N'-dioctadecylethylenediamine are dissolved in 2 ml of a mixture of trifluoroacetic acid and methylene chloride (1:3 v/v). After two hours, the mixture is subject to rotary evaporation and dried for 2 hours under a high vacuum. The residue is then taken up in 20 ml of chloroform, and 1 ml (920 mg, 4.5 mmol, MW 101.15, d=0.92) of 4-methylmorpholine is added. 640 mg (2.68 mmol, MW 238.13) of N-(tert-butoxycarbonyl)-3-bromopropylamine are then added. After boiling for 48 hours under reflux, the whole is concentrated by rotation and the BOC-protected precursor product is purified by flash chromatography. The product is then dissolved in 2 ml of a mixture of trifluoroacetic acid and methylene chloride (1:3 v/v), concentrated by rotary evaporation and lyophilised.

$C_{44}H_{94}N_4 \cdot 4\ CF_3COOH$
MW 679.21 (+4×114=1135.21)
MS (ESI): 680.2
Yield: 46 mg (13%)

Synthesis of N,N',N'-tris(cyanoethyl)-ornithine 950 mg of sodium hydroxide are dissolved in 20 ml of water. 2 g (11.86 mmol, MW 168.62) of ornithine hydrochloride are dissolved in the sodium hydroxide solution. Subsequently, 3 ml (45.57 mmol) of acrylonitrile are added dropwise and the whole is stirred at room temperature for 24 hours. After the addition of 1.7 ml of 25% hydrochloric acid a solid precipitates. This is suction-filtered off after cooling.

$C_{14}H_{21}O_2N_5 \cdot HCl$
MW 327.82
$R_f$=0.71 (1:1:1 v/v/v isopropanol/ethanol/water)
$^1H$ NMR (D$_2$O): 1.58 (m, 2H, C$\underline{H}_2$—CH$_{om}$); 1.90 (m, 2H, CH$_{2om}$); 2.61 (m, 6H, NC—C$\underline{H}_2$); 2.86 (tr, 4H, N—CH$_2$); 2.98 (tr, 2H, N—CH$_2$—C$\underline{H}_2$); 3.39 (tr, 2H, N—CH$_2$); 3.68 (tr, 1H, CH$_{om}$).
Yield: 2.1 g (54%)

Synthesis of N,N,N',N'-tetra(cyanoethyl)-ornithine 980 mg of sodium hydroxide are dissolved in 20 ml of water. 2 g (11.86 mmol, MW 168.62) of ornithine hydrochloride are dissolved in the sodium hydroxide solution. Subsequently, 3.9 ml (59.3 mmol) of acrylonitrile are added dropwise and the whole is stirred at room temperature for 8 days. A further 3 ml of acrylonitrile is then added dropwise, and the whole is stirred for a further 6 hours. After the addition of 1.7 ml of 25% hydrochloric acid the product is extracted by shaking with ethyl acetate three times. The organic phase is dried over sodium sulphate and concentrated by rotary evaporation.

$C_{17}H_{24}O_2N_6 \cdot HCl$
MW 344.4182
$R_f$=0.84 (1:1:1 v/v/v isopropanol/ethanol/water)
$^1H$ NMR (D$_2$O): 1.60 (m, 2H, C$\underline{H}_2$—CH$_{om}$); 1.92 (m, 2H, CH$_{2om}$); 2.52 (m, 8H, NC—C$\underline{H}_2$); 2.61 (tr, 4H, CH$_{2om}$); 2.87 (tr, 4H, N—CH$_2$); 3.03 (tr, 4H, N—CH$_2$); 3.38 (m, 1H, CH$_{om}$).
Yield: 2.4 g (59%)

Example 4
Liposome/micelle Formulation

Dioleoyl phosphatidyl ethanolamine, dioleoyl phosphatidyl choline, cholesterol or cholesteryl amine are dissolved in an organic solvent (e.g. chloroform). The lipid from Example 1 is dissolved per se or in the form of a salt, for example a trifluoroacetate salt, in an organic solvent (for example chloroform). By combining various amounts of the different solutions, different compositions of colipids and cationic lipid are produced. In a glass flask, a thin lipid film is produced by means of a rotary evaporator. The film is freed of solvent residues under a high vacuum. The film is hydrated with sufficient water or aqueous buffer solution to produce a concentration of 2 mg of lipid per ml of solution. Subsequently, with cooling, treatment is carried out with ultrasound (3×15 min.). The formulation is sterile-filtered through a filter (pore diameter 0.2 μm).

Example 5
Lipid Solutions

The lipids, per se or in the form of their TFA salts, are dissolved with or without colipids in ethanol. By mixing with water, solutions of various compositions are obtained.

Example 6
Cell Cultures

The cell lines CV-1, Hela S3 and NIH 3T3 are cultured in an incubator (5% CO$_2$ atmosphere) in Dulbecco's modified Eagle's medium (DMEM), which contains 10% foetal calf serum (FCS), 2 mM L-glutamine (Gln), 0.1 mM non-essential amino acids (NEAA), 100 U/ml penicillin and 100 μg/ml streptomycin.

Example 7

Transfection

The cells are plated out on a 12-well microtitre plate at a density of 1–1.5×10$^5$ and incubated overnight to approximately 60–80% confluence. In order to transfect the cells in a well, 1.5 μg of pCMV<Sport>β-Gal are dissolved in 50 μl of serum- and antibiotic-free DMEM. The cationic lipid (for example 3, 6, 9, 12 μl), in the form of ethanolic solution or liposome formulation, is also dissolved in 50 μl of serum- and antibiotic-free DMEM. The two solutions are mixed in a polystyrene container and left to stand for 10 to 15 minutes to allow the formation of the lipid/DNA complex.

In the meantime, the cells are washed once with PBS (phosphate-buffered saline). Depending on the desired conditions (transfection in serum-free or serum-containing medium), 0.4 ml of antibiotic-free DMEM with or without serum is added to the cells. The DNA/lipid complex is added directly to the cells and they are incubated for 6 hours in an incubator. Subsequently, the whole is made up to 1 ml with serum- and antibiotic-containing DMEM so that the medium has a final concentration of 10% serum. The cells are cultured for a further 20 hours. Testing for β-galactosidase is then performed according to the specifications of the manufacturer of the β-galactosidase assay kit. The o-nitrophenol that has developed is measured photometrically at 405 nm.

Results

The following Table and the following bar chart show a comparison of transfection efficiencies in the example of Hela S3 cells.

Transfection Reagent 1

N-[2,5-bis((3-aminopropyl)amino)-1-oxopentyl]-N',N'-dioctadecylethylenediamine (TFA salt) was used in the form of a liposome formulation with 25 mol % of dioleoyl phosphatidyl ethanolamine in aqueous sterile solution. Total amount of lipid: 2 mg/ml.

Transfection Reagent 2

N',N'-bis(3-aminopropyl)-N,N-dioctadecylethylenediamine (TFA salt) was used in the form of a liposome formulation with 50 mol % of dioleoyl phosphatidyl ethanolamine in aqueous sterile solution. Total amount of lipid: 2 mg/ml.

Transfection Reagent 3

Lipofectamin™ (Gibco-BRL: Life Technologies) was obtained from the manufacturer.

Absorption values at 405 nm:

| | Transfection reagent 1 | | Transfection reagent 2 | | Transfection reagent 3 | |
|---|---|---|---|---|---|---|
| | with serum | without serum | with serum | without serum | with serum | without serum |
| 3 μl | 1.61 | 1.92 | 0.63 | 1.65 | 0.81 | 1.93 |
| 6 μl | 2.40 | 2.40 | 0.71 | 0.80 | 0.30 | 1.65 |
| 9 μl | 2.10 | 1.68 | 0.95 | 0.58 | 0.19 | 0.44 |

Relative Transfection Efficiencies

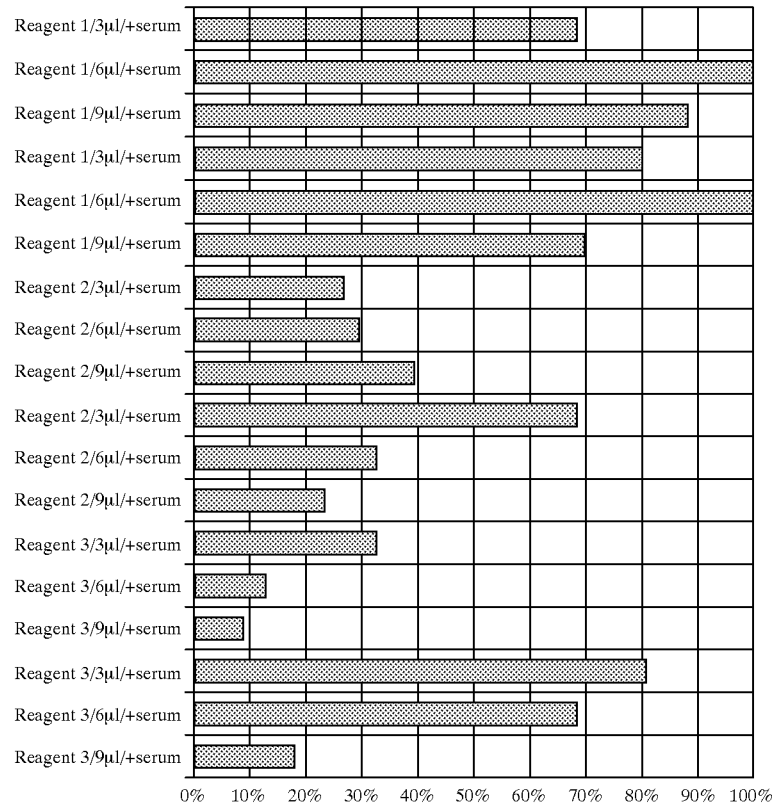

What is claimed is:

1. A compound corresponding to the following formula (I):

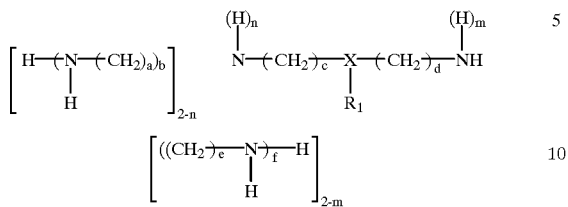

which, when a center of asymmetry is present, may occur in the D-, L- or DL-form, which includes salts thereof, wherein "$R_1$" is a lipophilic radical of the following general formula:

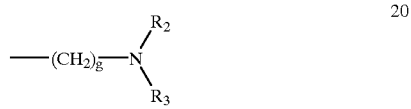

in which "$R_2$" and "$R_3$" are, independently, selected from the group consisting of dodecyl, dodecenyl, tetradecyl, tetradecenyl, hexadecyl, hexadecenyl, octadecyl, octadecenyl, and other alkyl radicals, and may be either saturated or unsaturated, branched or unbranched, fluorinated or non-fluorinated, and are constructed from 5 to 30 carbon atoms, wherein "X" is selected from one of the following formulae

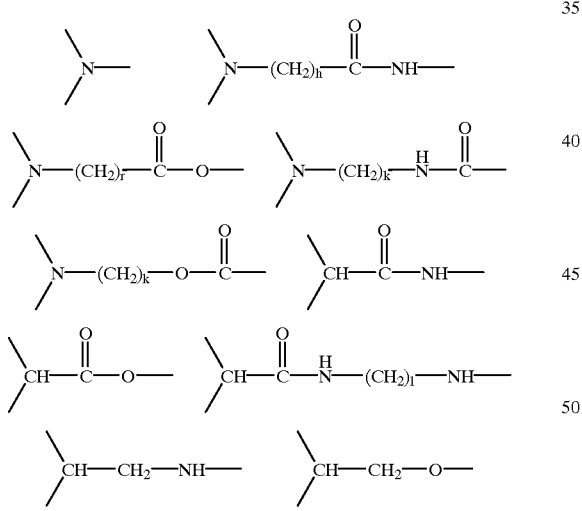

wherein, "m" is a number from 0 to 2, "n" is a number from 0 to 2, "g" is a number from 1 to 8, "a" is number from 0 to 6, "b" is a number from 0 to 6, "c" is a number from 0 to 6, "d" is a number from 0 to 6, "e" is a number from 0 to 6, "f" is a number from 0 to 6, "h" is a number from 0 to 6, "r" is a number from 0 to 6, "k" is a number from 0 to 6, and "l" is a number from 0 to 6, with the proviso that "b" is less than or equal to 1 whenever "a" equals 0, and "f" is less than or equal to 1 whenever "e" equals 0.

2. A compound according to claim 1 corresponding to one of the following structures:

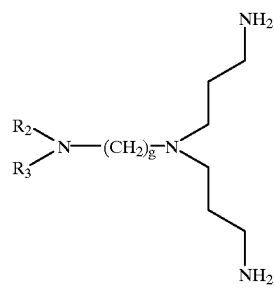

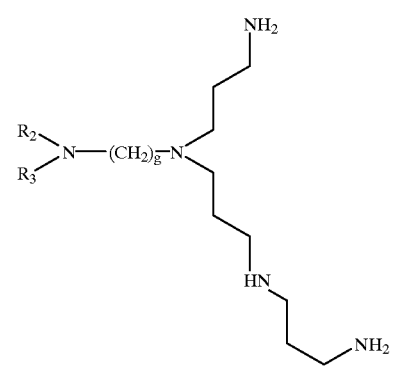

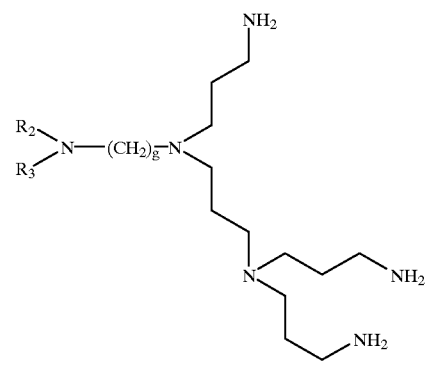

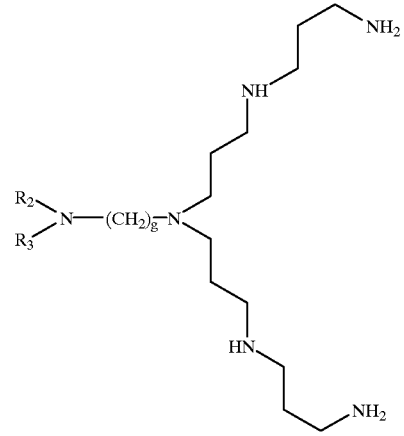

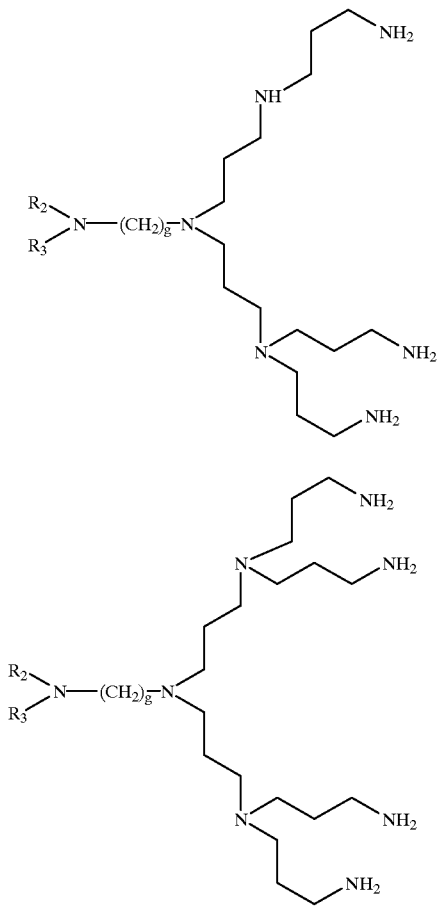
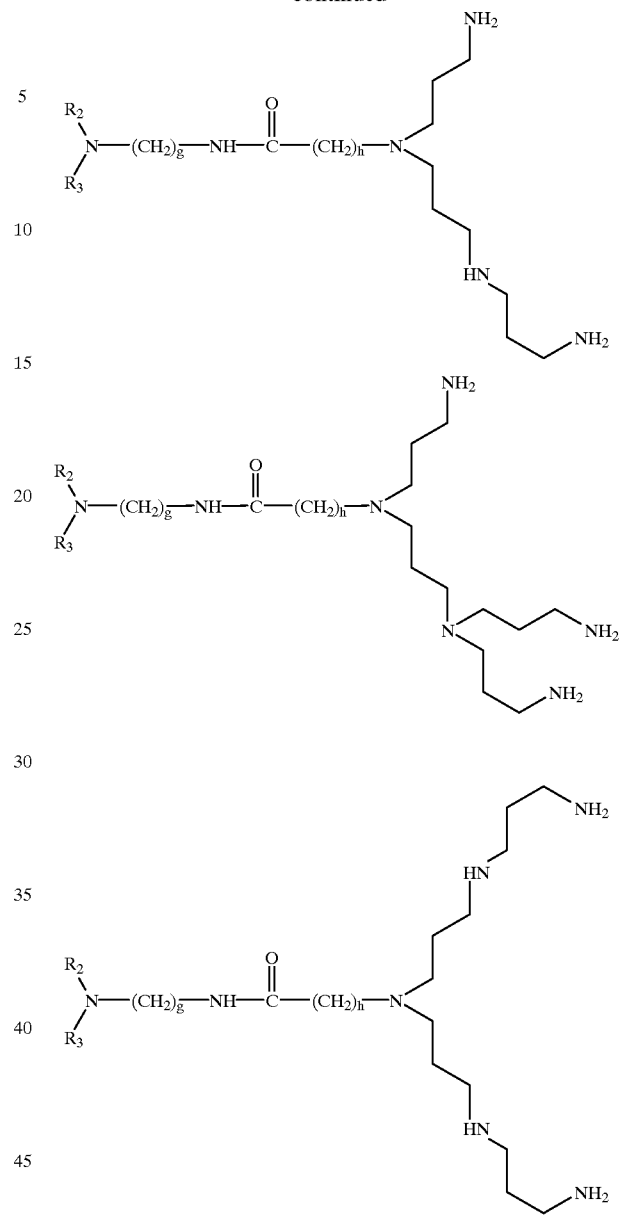
wherein "g" is a number from 1 to 8 and "$R_2$" and "$R_3$" are, independently, selected from the group consisting of dodecyl, dodecenyl, tetradecyl, tetradecenyl, hexadecyl, hexadecenyl, octadecyl and octadecenyl.
3. A compound according to claim 1 corresponding to one of the following structures:
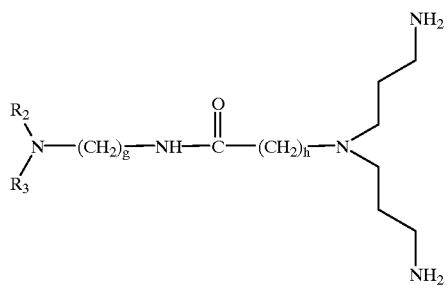
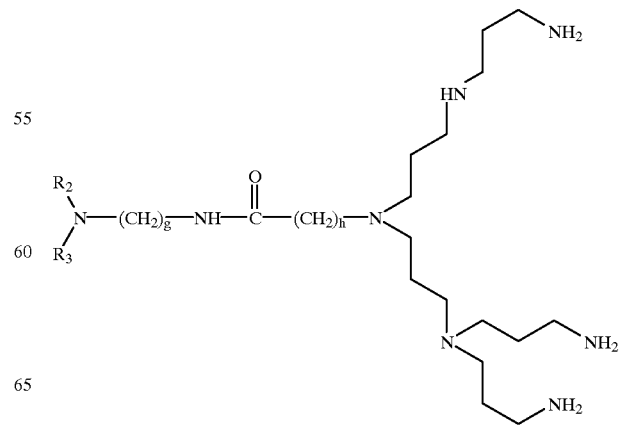

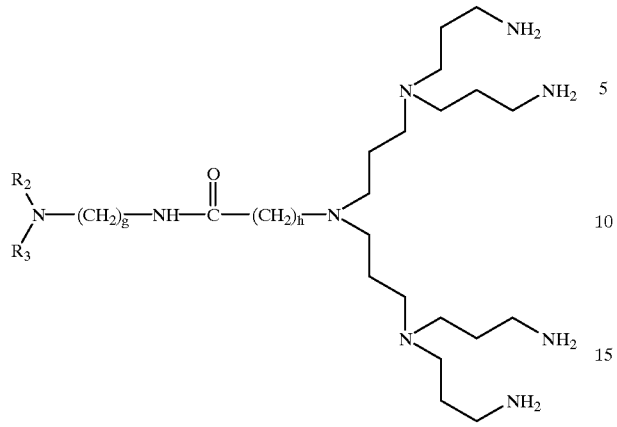

wherein "h" is a number from 0 to 6, "g" is a number from 1 to 8, and "R₂" and "R₃" are, independently, selected from the group consisting of dodecyl, dodecenyl, tetradecyl, tetradecenyl, hexadecyl, hexadecenyl, octadecyl and octadecenyl.

4. A compound according to claim 1 corresponding to one of the following structures:

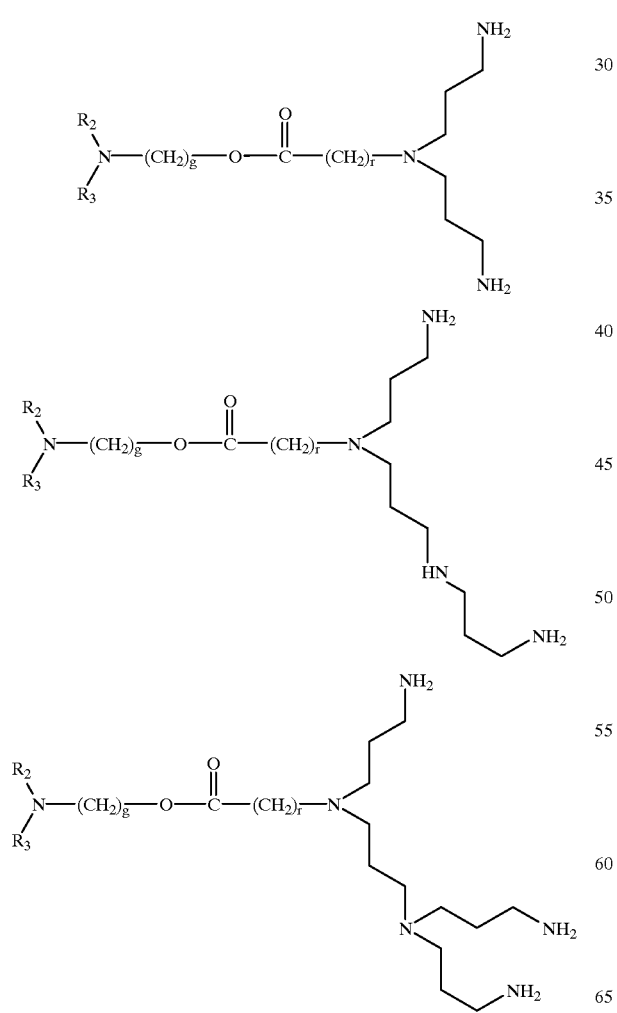

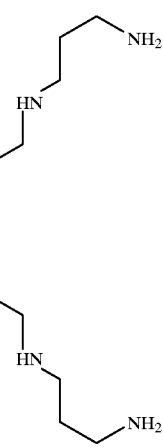

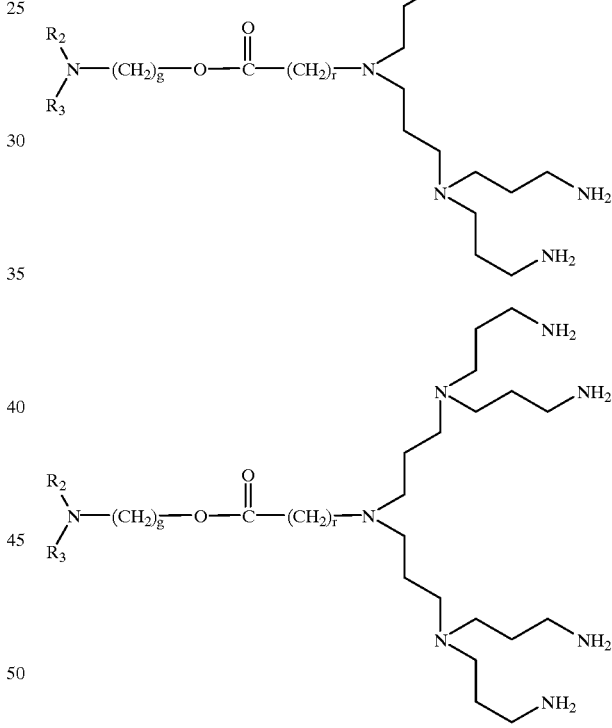

wherein "r" is a number from 0 to 6, "g" is number from 1 to 8, and "R₂" and "R₃", independently are selected from the group consisting of dodecyl, dodecenyl, tetradecyl, tetradecenyl, hexadecyl, hexadecenyl, octadecyl and octadecenyl.

5. A compound according to claim 1 corresponding to one of the following structures:

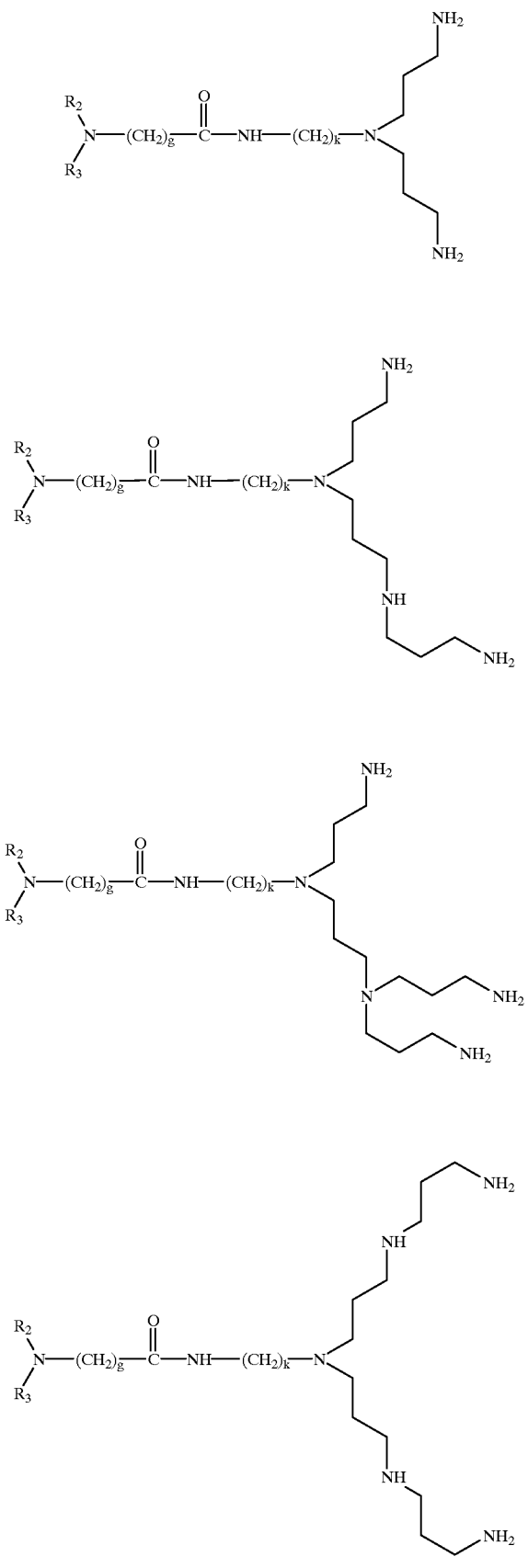
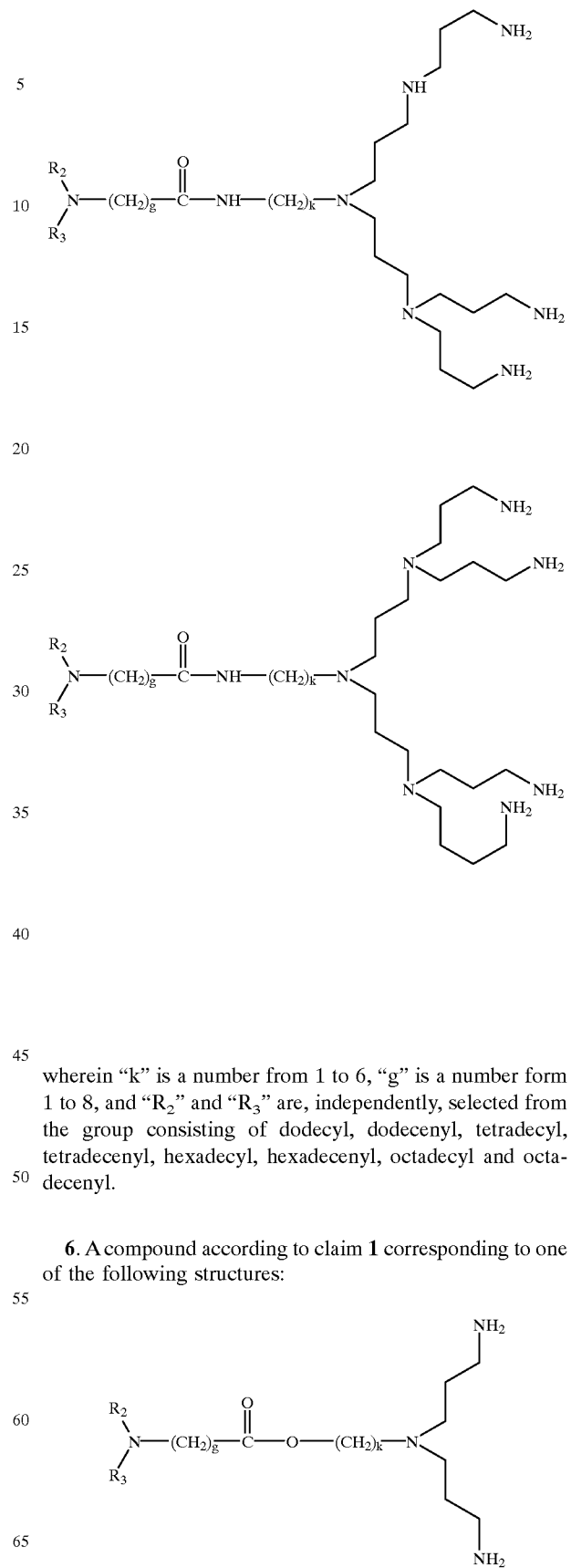
wherein "k" is a number from 1 to 6, "g" is a number form 1 to 8, and "R$_2$" and "R$_3$" are, independently, selected from the group consisting of dodecyl, dodecenyl, tetradecyl, tetradecenyl, hexadecyl, hexadecenyl, octadecyl and octadecenyl.
6. A compound according to claim 1 corresponding to one of the following structures:

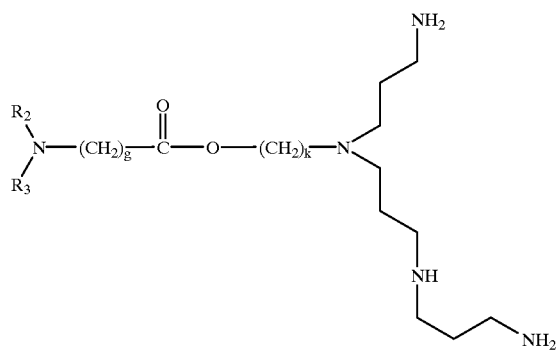
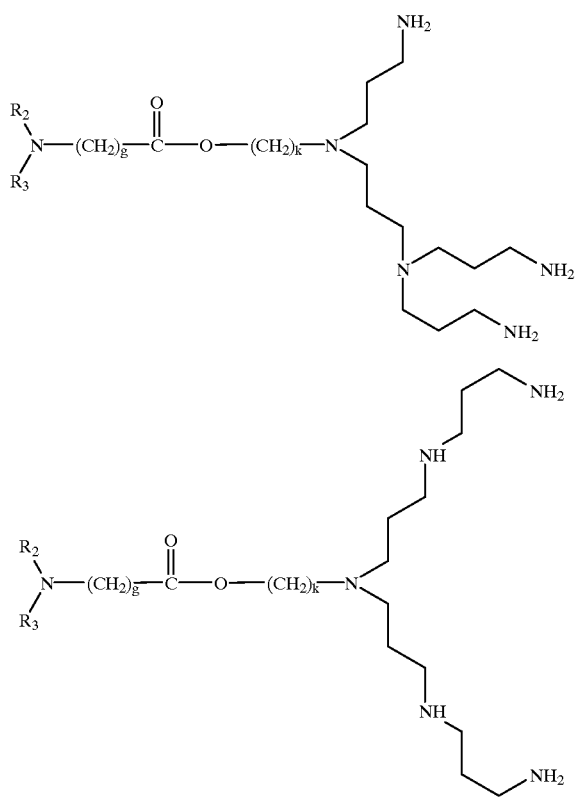
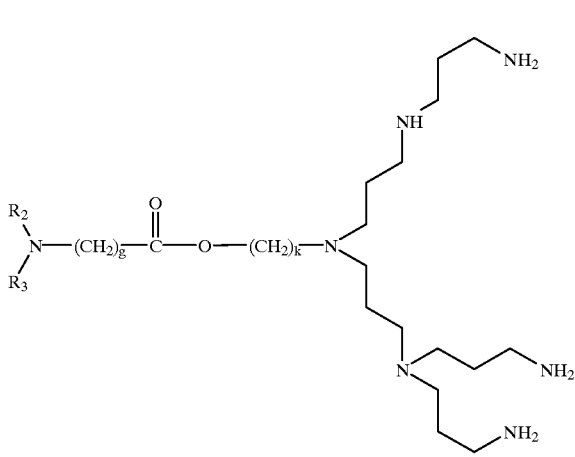

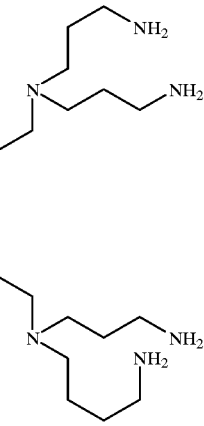

wherein "k" is a number from 1 to 6, "g" is a number form 1 to 8, and "R$_2$" and "R$_3$" are, independently, selected from the group consisting of dodecyl, dodecenyl, tetradecyl, tetradecenyl, hexadecyl, hexadecenyl, octadecyl and octadecenyl.

7. A compound according to claim 1 corresponding to one of the following structures:

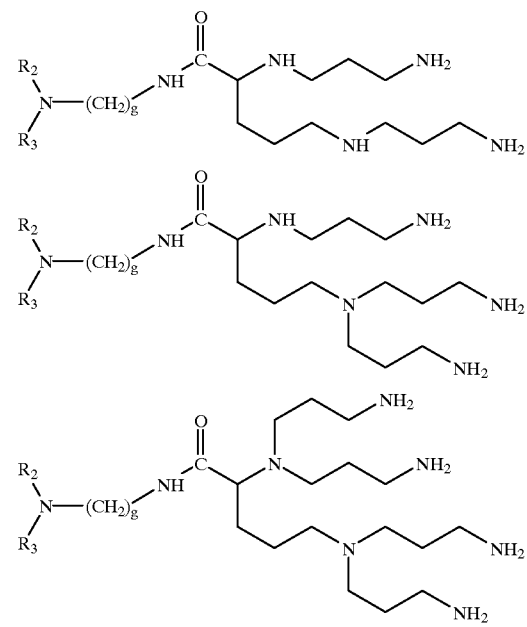

wherein "g" is a number from 1 8 and "R$_2$" and "R$_3$" are, independently selected from the group consisting of dodecyl, dodecenyl, tetradecyl, tetradecenyl, hexadecyl, hexadecenyl, octadecyl and octadecenyl.

8. A compound according to claim 1 corresponding to one of the following structures:

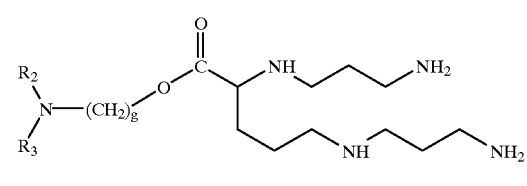

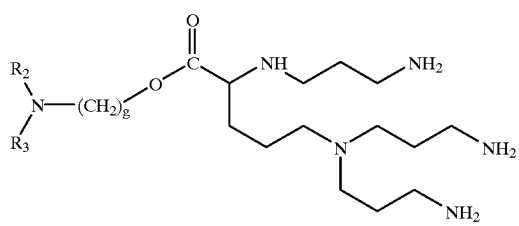

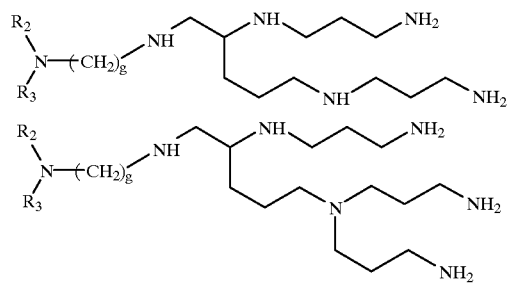

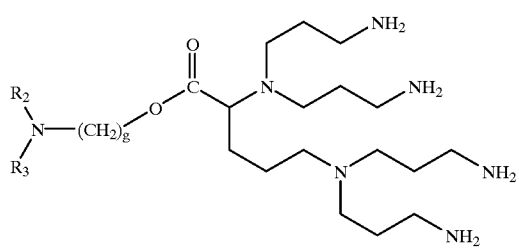

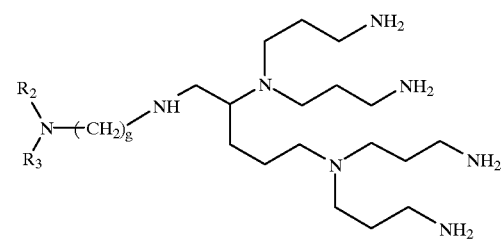

wherein "g" is a number from 1 to 8 and "R₂" and "R₃" are, independently, selected from the group consisting of dodecyl, dodecenyl, tetradecyl, tetradecenyl, hexadecyl, hexadecenyl, octadecyl and octadecenyl.

9. A compound according to claim 1 corresponding to one of the following structures:

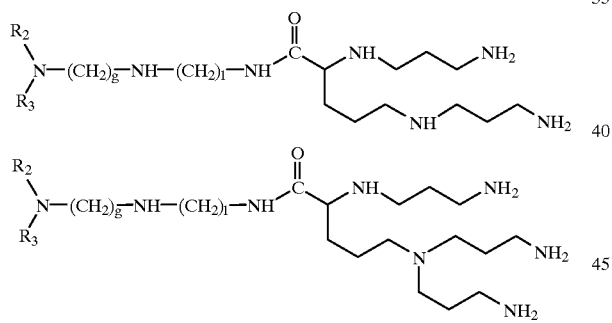

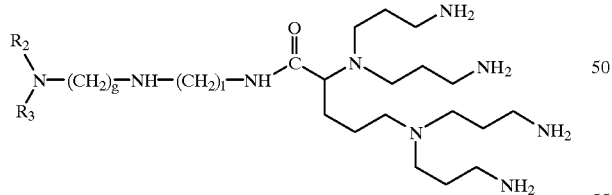

wherein "g" is a number from 1 to 8, and R₂ and R₃ are, independently, selected from the group consisting of dodecyl, dodecenyl, tetradecyl, tetradecenyl, hexadecyl, hexadecenyl, octadecyl and octadecenyl.

11. A compound according to claim 1 corresponding to one of the following structures:

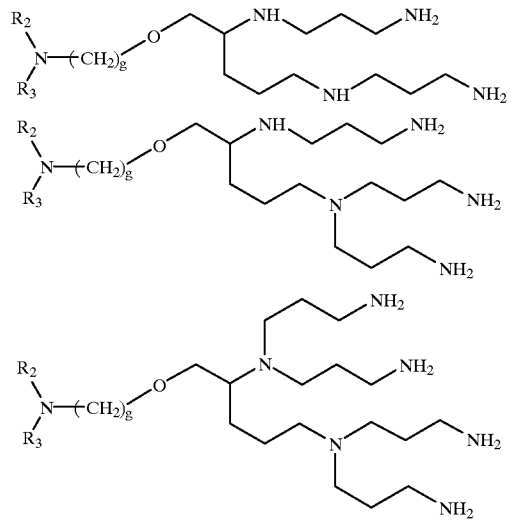

wherein "l" is a number from 0 to 6, "g" is a number from 1 to 8, and "R₂" and "R₃" are, independently, selected from the group consisting of dodecyl, dodecenyl, tetradecyl, tetradecenyl, hexadecyl, hexadecenyl, octadecyl and octadecenyl.

10. A compound according to claim 1 corresponding to one of the following structures:

wherein "g" is a number from 1 to 8, and R₂ and R₃ are, independently, selected from the group consisting of dodecyl, dodecenyl, tetradecyl, tetradecenyl, hexadecyl, hexadecenyl, octadecyl and octadecenyl.

12. A compound according to claim 1 corresponding to one of the following structures:

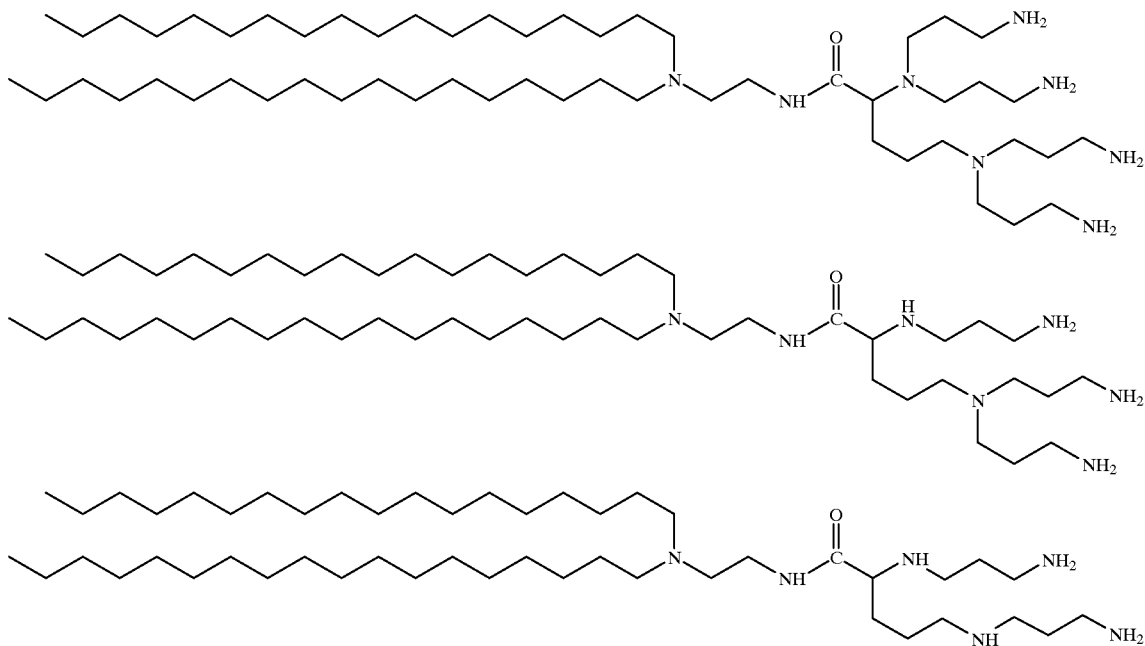

13. A medicinal or diagnostic composition comprising:
   a compound from claim 1;
   a colipid; and
   optionally, customary additives, carriers and/or adjuvants.

14. A method of introducing biologically active compounds into eukaryotic cells comprising the followings steps:

complexing a biologically active compound with a compound from claim 1; and contacting the resulting complexes (in vivo or) in vitro with eukaryotic cells.

* * * * *